US008852926B2

(12) United States Patent
Mo et al.

(10) Patent No.: US 8,852,926 B2
(45) Date of Patent: Oct. 7, 2014

(54) GENETIC SELECTION SYSTEM FOR IDENTIFICATION OF MICRORNA TARGET GENES

(75) Inventors: Yin-Yuan Mo, Springfield, IL (US); Fangting Wu, Springfield, IL (US)

(73) Assignee: Board of Trustees of Southern Illinois University, Carbondale, IL (US)

( * ) Notice: Subject to any disclaimer, the term of this patent is extended or adjusted under 35 U.S.C. 154(b) by 1074 days.

(21) Appl. No.: 12/258,016

(22) Filed: Oct. 24, 2008

(65) Prior Publication Data

US 2009/0137421 A1  May 28, 2009

Related U.S. Application Data

(60) Provisional application No. 61/000,336, filed on Oct. 25, 2007.

(51) Int. Cl.
*C12N 15/00* (2006.01)
*C40B 30/06* (2006.01)
*C12N 15/11* (2006.01)

(52) U.S. Cl.
CPC .......... *C12N 15/111* (2013.01); *C12N 2320/11* (2013.01); *C12N 2320/12* (2013.01); *C12N 2310/141* (2013.01)
USPC ........................................ 435/320.1; 506/10

(58) Field of Classification Search
USPC .......................................... 435/320.1; 506/10
See application file for complete search history.

(56) References Cited

PUBLICATIONS

Pillai RS MicroRNA function: multiple mechanisms for a tiny RNA? RNA, 2005; vol. 11, pp. 1753-1761, copyright by RNA Society.
Zamore PD, Haley B Ribo-gnome: the big world of small RNAs. Science, 2005; vol. 309, pp. 1519-1524.
Bartel DP MicroRNAs: genomics, biogenesis, mechanism, and function. Cell, 2004; vol. 116, pp. 281-297, copyright by Cell Press.
Berezikov E, Guryev V, van de Belt J, Wienholds E, Plasterk RH, Cuppen E Phylogenetic shadowing and computational identification of human microRNA genes. Cell, 2005; vol. 120, pp. 21-24, copyright by Elsevier Inc.
Lee RC, Feinbaum RL, Ambros V The *C. elegans* heterochronic gene lin-4 encodes small RNAs with antisense complementarity to lin-14. Cell, 1993; vol. 75, pp. 843-854, copyright by Cell Press.
Wightman B, Ha I, Ruvkun G Posttranscriptional regulation of the heterochronic gene lin-14 by lin-4 mediates temporal pattern formation in *C. elegans*. Cell, 1993; vol. 75, pp. 855-862, copyright by Cell Press.
Reinhart BJ.Slack FJ.Basson M.Pasquinelli AE.Bettinger JC.Rougvie AE, et al. The 21-nucleotide let-7 RNA regulates developmental timing in *Caenorhabditis elegans*. Nature, 2000; vol. 403, pp. 901-906, copyright by Macmillan Magazines Ltd.
Griffiths-Jones S, Saini HK, van Dongen S, Enright AJ miRBase: tools for microRNA genomics. Nucleic Acids Research, 2007; vol. 36, pp. D154-D158, copyright by The Aughors.
Kim VN MicroRNA biogenesis: coordinated cropping and dicing. Nature Reviews Molecular Cell Biology, 2005; vol. 6, pp. 376-385.
Yi R, Qin Y, Macara IG, Cullen BR Exportin-5 mediates the nuclear export of pre-microRNAs and short hairpin RNAs. Genes & Development, 2003; vol. 17, pp. 3011-3016, copyright by Cold Spring Harbor Laboratory Press.
Du T, Zamore PD microPrimer: the biogenesis and function of microRNA. Development, 2005; vol. 132, pp. 4645-4652.
Esquela-Kerscher A, Slack FJ OncomiRs—microRNAs with a role in cancer. Nature Reviews Cancer, 2006; vol. 6, pp. 259-269, copyright by Nature Publishing Group.
Brennecke J, Stark A, Russell RB, Cohen SM Principles of microRNA-target recognition. PLoS Biology, 2005; vol. 3, Issue 3, e85, pp. 0404-0418, copyright by Brennecke et al.
Lewis BP, Burge CB, Bartel DP Conserved seed pairing, often flanked by adenosines, indicates that thousands of human genes are microRNA targets. Cell, 2005; vol. 120, pp. 15-20, copyright by Elsevier Inc.
Hobert O Gene regulation by transcription factors and microRNAs. Science, 2008; vol. 319, pp. 1785-1786.
Lu J.Getz G.Miska EA.Alvarez-Saavedra E.Lamb J.Peck D, et al. MicroRNA expression profiles classify human cancers. Nature, 2005; vol. 435, pp. 834-838, copyright by Nature Publishing Group.
Calin GA.Ferracin M.Cimmino A.Di Leva G.Shimizu M.Wojcik SE, et al. A MicroRNA signature associated with prognosis and progression in chronic lymphocytic leukemia. The New England Journal of Medicine, 2005; vol. 353, pp. 1793-1801, copyright by Massachusetts Medical Society.
Yanaihara N.Caplen N.Bowman E.Seike M.Kumamoto K.Yi M, et al. Unique microRNA molecular profiles in lung cancer diagnosis and prognosis. Cancer Cell, 2006; vol. 9, pp. 189-198, copyright by Elsevier Inc.
Bottoni A.Zatelli MC.Ferracin M.Tagliati F.Piccin D.Vignali C, et al. Identification of differentially expressed microRNAs by microarray: a possible role for microRNA genes in pituitary adenomas. Journal of Cellular Physiology, 2007; vol. 210, pp. 370-377, copyright by Wiley-Liss Inc.
Wang T.Zhang X.Obijuru L.Laser J.Aris V.Lee P, et al. A micro-RNA signature associated with race, tumor size, and target gene activity in human uterine leiomyomas. Genes, Chromosomes, & Cancer, 2007; vol. 46, pp. 336-347, copyright by Wiley-Liss Inc.
Debernardi S, Skoulakis S, Molloy G, Chaplin T, Dixon-McIver A, Young BD MicroRNA miR-181a correlates with morphological subclass of acute myeloid leukaemia and the expression of its target genes in global genome-wide analysis. Leukemia, 2007; vol. 21, pp. 912-916, copyright by Nature Publishing Group.
Lee EJ.Gusev Y.Jiang J.Nuovo GJ.Lerner MR.Frankel WL, et al. Expression profiling identifies microRNA signature in pancreatic cancer. International Journal of Cancer, 2007; vol. 120, pp. 1046-1054, copyright by Wiley-Liss Inc.

(Continued)

*Primary Examiner* — Jon E Angell

(74) *Attorney, Agent, or Firm* — Mark Stallion; Husch Blackwell LLP

(57) ABSTRACT

There is provided an expression cassette comprising a 3'-UTR cDNA library fragment, mammalian cells transfected with the expression cassette, and kits comprising the same. Furthermore, methods for identifying target genes for microRNAs are provided that utilize the expression cassette hereof.

35 Claims, 15 Drawing Sheets

(56) References Cited

PUBLICATIONS

Volinia S.Calin GA.Liu CG.Ambs S.Cimmino A.Petrocca F, et al. A microRNA expression signature of human solid tumors defines cancer gene targets. Proceedings of the National Academy of Sciences USA, 2006; vol. 103, pp. 2257-2261, copyright by the National Academy of Sciences of the USA.

Dostie J, Mourelatos Z, Yang M, Sharma A, Dreyfuss G Numerous microRNPs in neuronal cells containing novel microRNAs. RNA, 2003; vol. 9, pp. 180-186, copyright by TNA Society.

Hwang HW, Mendell JT MicroRNAs in cell proliferation, cell death, and tumorigenesis. British Journal of Cancer, 2006; vol. 94, pp. 776-780, copyright by Cancer Research UK.

Croce CM, Calin GA miRNAs, cancer, and stem cell division. Cell, 2005; vol. 122, pp. 6-7.

Hammond SM MicroRNAs as oncogenes. Current Opinion in Genetics & Development, 2006; vol. 16, pp. 4-9, copyright by Elsevier Ltd.

Gregory RI, Shiekhattar R MicroRNA biogenesis and cancer. Cancer Research, 2005; vol. 65, No. 9, pp. 3509-3512, copyright by American Association for Cancer Research.

Chen CZ MicroRNAs as oncogenes and tumor suppressors. The New England Journal of Medicine, 2005; vol. 353, pp. 1768-1771.

Calin GA.Liu CG.Sevignani C.Ferracin M.Felli N.Dumitru CD, et al. MicroRNA profiling reveals distinct signatures in B cell chronic lymphocytic leukemias. Proceedings of the National Academy of Sciences USA, 2004; vol. 101, No. 32, pp. 11755-11760, copyright by the National Academy of Sciences of the USA.

Calin GA.Dumitru CD.Shimizu M.Bichi R.Zupo S.Noch E, et al. Frequent deletions and down-regulation of micro-RNA genes miR15 and miR16 at 13q14 in chronic lymphocytic leukemia. Proceedings of the National Academy of Sciences USA, 2002; vol. 99, No. 24, pp. 15524-15529.

Johnson SM.Grosshans H.Shingara J.Byrom M.Jarvis R.Cheng A, et al. RAS is regulated by the let-7 microRNA family. Cell, 2005; vol. 120, pp. 635-647, copyright by Elsevier Inc.

Cimmino A.Calin GA.Fabbri M.Iorio MV.Ferracin M.Shimizu M, et al. miR-15 and miR-16 induce apoptosis by targeting BCL2. Proceedings of the National Academy of Sciences USA, 2005; vol. 102, No. 39, pp. 13944-13949, copyright by the National Academy of Sciences of the USA.

O'Donnell KA, Wentzel EA, Zeller KI, Dang CV, Mendell JT c-Myc-regulated microRNAs modulate E2F1 expression. Nature, 2005; vol. 435, pp. 839-843, copyright by Nature Publishing Group.

He L.Thomson JM.Hemann MT.Hernando-Monge E.Mu D.Goodson S, et al. A microRNA polycistron as a potential human oncogene. Nature, 2005; vol. 435, pp. 828-833, copyright by Nature Publishing Group.

Hayashita Y.Osada H.Tatematsu Y.Yamada H.Yanagisawa K.Tomida S, et al. A polycistronic microRNA cluster, miR-17-92, is overexpressed in human lung cancers and enhances cell proliferation. Cancer Research, 2005; vol. 65, No. 21, pp. 9628-9632, copyright by American Association for Cancer Research.

Voorhoeve PM.le Sage C.Schrier M.Gillis AJ.Stoop H.Nagel R, et al. A genetic screen implicates miRNA-372 and miRNA-373 as oncogenes in testicular germ cell tumors. Cell, 2006; vol. 124, pp. 1169-1181, copyright by Elsevier Inc.

Si ML, Zhu S, Wu H, Lu Z, Wu F, Mo YY miR-21-mediated tumor growth. Oncogene, 2007; vol. 26, pp. 2799-2803.

Chan JA, Krichevsky AM, Kosik KS MicroRNA-21 is an antiapoptotic factor in human glioblastoma cells. Cancer Research, 2005; vol. 65, No. 14, pp. 6029-6033, copyright by American Association for Cancer Research.

Zhu S, Si ML, Wu H, Mo YY MicroRNA-21 targets the tumor suppressor gene tropomyosin 1 (TPM1). The Journal of Biological Chemistry, 2007; vol. 282, No. 19, pp. 14328-14336, copyright by The American Society for Biochemistry and Molecular Biology, Inc.

Zhu S, Wu H, Wu F, Nie D, Sheng S, Mo YY MicroRNA-21 targets tumor suppressor genes in invasion and metastasis. Cell Research, 2008; vol. 18, pp. 350-359, copyright by IBCB, SIBS, CAS.

Ma L, Teruya-Feldstein J, Weinberg RA Tumour invasion and metastasis initiated by microRNA-10b in breast cancer. Nature, 2007; vol. 449, pp. 682-688, copyright by Nature Publishing Group.

Tavazoie SF.Alarcon C.Oskarsson T.Padua D.Wang Q.Bos PD, et al. Endogenous human microRNAs that suppress breast cancer metastasis. Nature, 2008; vol. 451, pp. 147-152, copyright by Nature Publishing Group.

Stark A, Brennecke J, Russell RB, Cohen SM Identification of *Drosophila* MicroRNA targets. PLoS Biology, 2003; vol. 1, Issue 3, pp. 397-409, copyright by Stark et al.

Lewis BP, Shih IH, Jones-Rhoades MW, Bartel DP, Burge CB Prediction of mammalian microRNA targets. Cell, 2003; vol. 115, pp. 787-798, copyright by Cell Press.

Kiriakidou M, Nelson PT, Kouranov A, Fitziev P, Bouyioukos C, Mourelatos Z, et al. A combined computational-experimental approach predicts human microRNA targets. Genes & Development, 2004; vol. 18, pp. 1165-1178, copyright by Cold Spring Harbor Laboratory Press.

Didiano D, Hobert O Perfect seed pairing is not a generally reliable predictor for miRNA-target interactions. Nature Structural & Molecular Biology, 2006; vol. 13, No. 9, pp. 849-851, copyright by Nature Publishing Group.

Didiano D, Hobert O Molecular architecture of a miRNA-regulated 3' UTR. RNA, 2008; vol. 14, pp. 1297-1317, copyright by RNA Society.

Grimson A, Farh KK, Johnston WK, Garrett-Engele P, Lim LP, Bartel DP MicroRNA targeting specificity in mammals: determinants beyond seed pairing. Molecular Cell, 2007; vol. 27, pp. 91-105, copyright by Elsevier Inc.

Krek A.Grun D.Poy MN.Wolf R.Rosenberg L.Epstein EJ, et al. Combinatorial microRNA target predictions. Nature Genetics, 2005; vol. 37, No. 5, pp. 495-500, copyright by Nature Publishing Group.

John B, Enright AJ, Aravin A, Tuschl T, Sander C, Marks DS Human MicroRNA targets. PLoS Biology, 2004; vol. 2, Issue 11, e363, pp. 1862-1879, copyright by John et al.

Long D, Lee R, Williams P, Chan CY, Ambros V, Ding Y Potent effect of target structure on microRNA function. Nature Structural & Molecular Biology, 2007; vol. 14, No. 4, pp. 287-294, copyright by Nature Publishing Group.

Huang JC.Babak T.Corson TW.Chua G.Khan S.Gallie BL, et al. Using expression profiling data to identify human microRNA targets. Nature Methods, 2007; vol. 4, No. 12, pp. 1045-1049, copyright by Nature Publishing Group.

Lim LP.Lau NC.Garrett-Engele P.Grimson A.Schelter JM.Castle J, et al. Microarray analysis shows that some microRNAs downregulate large numbers of target mRNAs. Nature, 2005; vol. 433, pp. 769-773, copyright by Nature Publishing Group.

Vatolin S, Navaratne K, Weil RJ A novel method to detect functional microRNA targets. Journal of Molecular Biology, 2006; vol. 358, pp. 983-996, copyright by Elsevier Ltd.

Karginov FV, Conaco C, Xuan Z, Schmidt BH, Parker JS, Mandel G, et al. A biochemical approach to identifying microRNA targets. Proceedings of the National Academy of Sciences USA, 2007; vol. 104, No. 49, pp. 19291-19296, copyright by the National Academy of Sciences of the USA.

Easow G, Teleman AA, Cohen SM Isolation of microRNA targets by miRNP immunopurification. RNA, 2007; vol. 13, pp. 1198-1204, copyright by RNA Society.

Beitzinger M, Peters L, Zhu JY, Kremmer E, Meister G Identification of human microRNA targets from isolated argonaute protein complexes. RNA Biology, 2007; vol. 4, Issue 2, pp. 76-84.

Zhang L.Ding L.Cheung TH.Dong MQ.Chen J.Sewell AK, et al. Systematic identification of *C. elegans* miRISC proteins, miRNAs, and mRNA targets by their interactions with GW182 proteins AIN-1 and AIN-2. Molecular Cell, 2007; vol. 28, pp. 598-613, copyright by Elsevier Inc.

Hendrickson DG, Hogan DJ, Herschlag D, Ferrell JE, Brown PO Systematic identification of mRNAs recruited to argonaute 2 by specific microRNAs and corresponding changes in transcript abundance. PLoS ONE 2008; vol. 3, Issue 5, e2126, pp. 1-15.

Mo YY, Wang C, Beck WT A novel nuclear localization signal in human DNA topoisomerase I. The Journal of Biological Chemistry,

(56) References Cited

OTHER PUBLICATIONS

2000; vol. 275, No. 52, pp. 41107-41113, copyright by The Americal Society for Biochemistry and Molecular Biology, Inc.

Wu F, Chiocca S, Beck WT, Mo YY Gam1-associated alterations of drug responsiveness through activation of apoptosis. Molecular Cancer Therapeutics, 2007; vol. 6, No. 6, pp. 1823-1830, copyright by American Association for Cancer Research.

Margolin JF, Friedman JR, Meyer WK, Vissing H, Thiesen HJ, Rauscher FJ, 3rd Kruppel-associated boxes are potent transcriptional repression domains. Proceedings of the National Academy of Sciences USA, 1994; vol. 91, pp. 4509-4513.

Deuschle U, Meyer WK, Thiesen HJ Tetracycline-reversible silencing of eukaryotic promoters. Molecular and Cellular Biology, 1995; vol. 15, No. 4, pp. 1907-1914, copyright by American Society for Microbiology.

Herchenroder O, Hahne JC, Meyer WK, Thiesen HJ, Schneider J Repression of the human immunodeficiency virus type 1 promoter by the human KRAB domain results in inhibition of virus production. Biochimica et Biophysica Acta, 1999; vol. 1445, pp. 216-223, copyright by Elsevier Science B.V.

Rittner K, Schultz H, Pavirani A, Mehtali M Conditional repression of the E2 transcription unit in E1-E3-deleted adenovirus vectors is correlated with a strong reduction in viral DNA replication and late gene expression in vitro. Journal of Virology, 1997; vol. 71, No. 4, pp. 3307-3311, copyright by American Society for Microbiology.

Cmarik JL.Min H.Hegamyer G.Zhan S.Kulesz-Martin M.Yoshinaga H, et al. Differentially expressed protein Pdcd4 inhibits tumor promoter-induced neoplastic transformation. Proceedings of the National Academy of Sciences USA, 1999; vol. 96, No. 24, pp. 14037-14042.

Lau AT, Chiu JF The possible role of cytokeratin 8 in cadmium-induced adaptation and carcinogenesis. Cancer Research, 2007; vol. 67, No. 5, pp. 2107-2113, copyright by American Association for Cancer Research.

Stark A, Brennecke J, Bushati N, Russell RB, Cohen SM Animal MicroRNAs confer robustness to gene expression and have a significant impact on 3'UTR evolution. Cell, 2005; vol. 123, pp. 1133-1146, copyright by Elsevier Inc.

Ørom UA, Nielsen FC, Lund AH, MicroRNA-10a binds the 5'UTR of ribosomal protein mRNAs and enhances their translation, Molecular Cell. May 23, 2008, vol. 30, No. 4, pp. 460-471, copyright by Elsevier Inc.

Forman JJ, Legesse-Miller A, Coller HA. A search for conserved sequences in coding regions reveals that the let-7 microRNA targets Dicer within its coding sequence. Proceedings of the National Academy of Sciences USA, Sep. 30, 2008, vol. 105, No. 39, pp. 14879-14884, copyright by the National Academy of Sciences of the USA.

Tay Y, Zhang J, Thomson AM, Lim B, Rigoutsos I. MicroRNAs to Nanog, Oct4 and Sox2 coding regions modulate embryonic stem cell differentiation. Nature, 2008. vol. 455, pp. 1124-1129, copyright by Macmillan Publishers Limited.

Baek D, Villén J, Shin C, Camargo FD, Gygi SP, Bartel DP, The impact of microRNAs on protein output, Nature. Sep. 4, 2008; vol. 455, No. 7209, pp. 64-71, Electronically published Jul. 30, 2008, copyright by Macmillan Publishers Limited.

Selbach M, Schwanhäusser B, Thierfelder N, Fang Z, Khanin R, Rajewsky N., Widespread changes in protein synthesis induced by microRNAs, Nature. Sep. 4, 2008; vol. 455, No. 7209, pp. 58-63. Electronically published Jul. 30, 2008, copyright by Macmillan Publishers Limited.

microRNA.org: A resource for predicted microRNA targets and expression. Copyright by Memorial Sloan-Kettering Cancer Center. Sep. 2008. http://www.microrna.org/microrna/home.do.

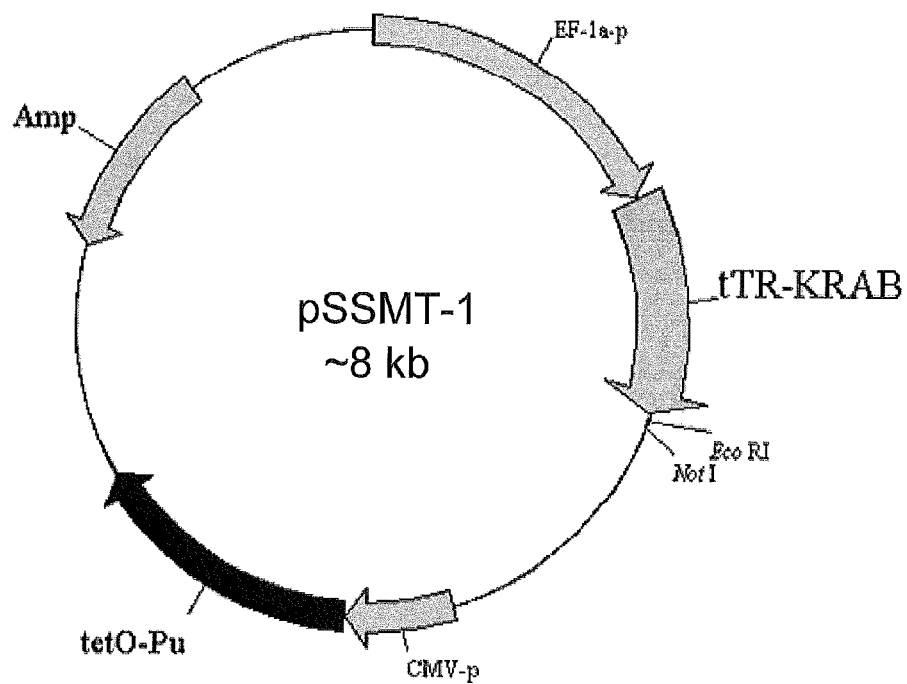
FIG. 1  Plasmid pSSMT1 carrying both tTR-KRAB and tetO-Pu.

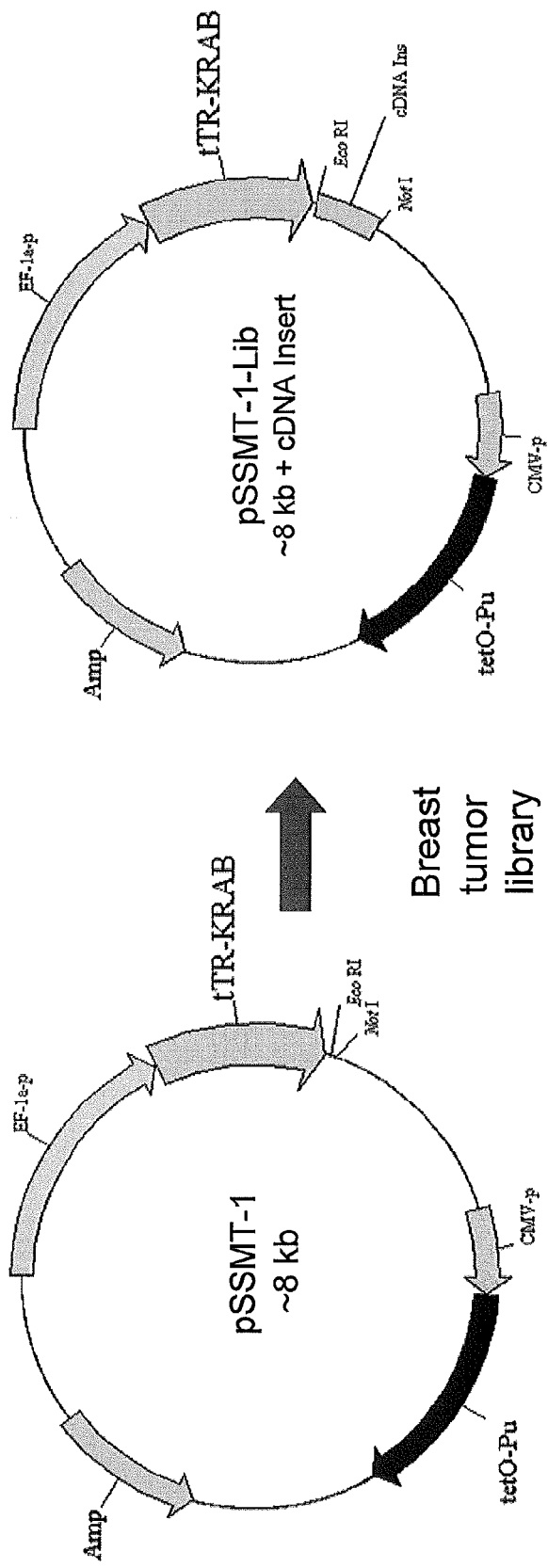
FIG. 2  Construction of pSSMT-1-lib.

Principle of the selection system

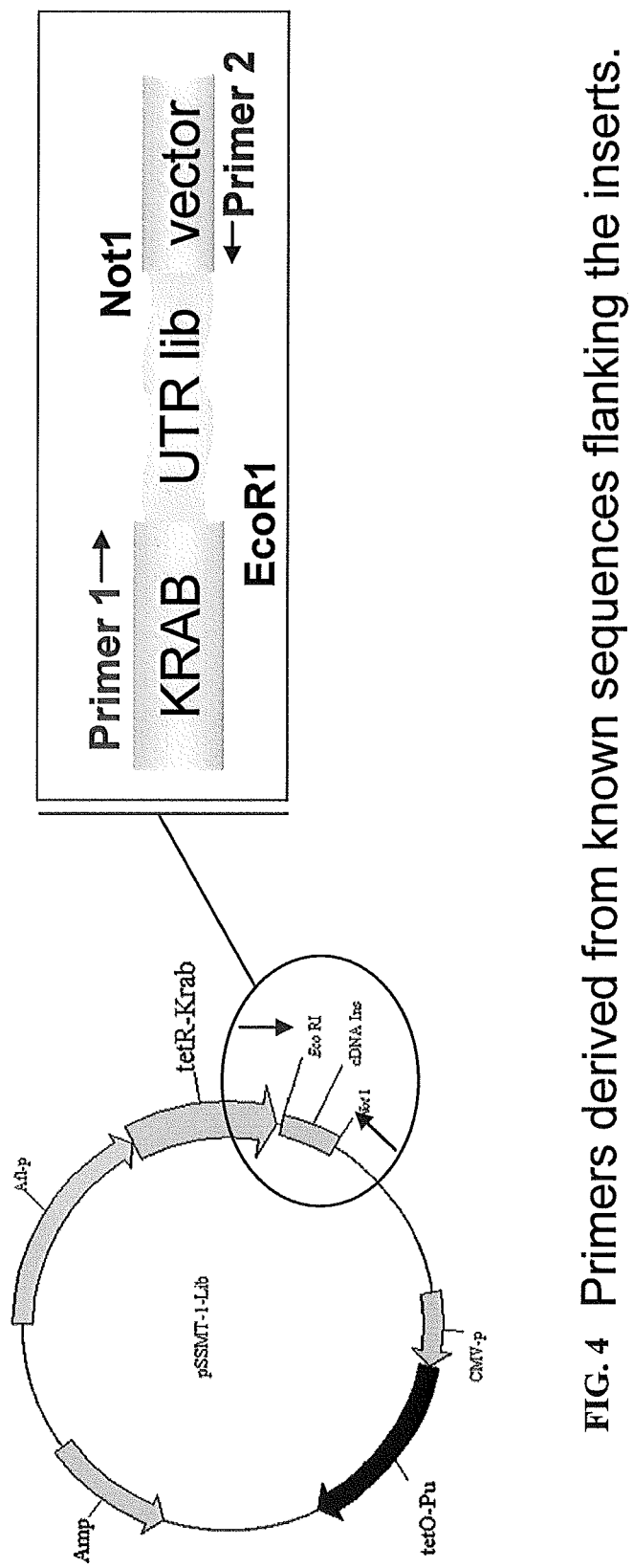
FIG. 4  Primers derived from known sequences flanking the inserts.

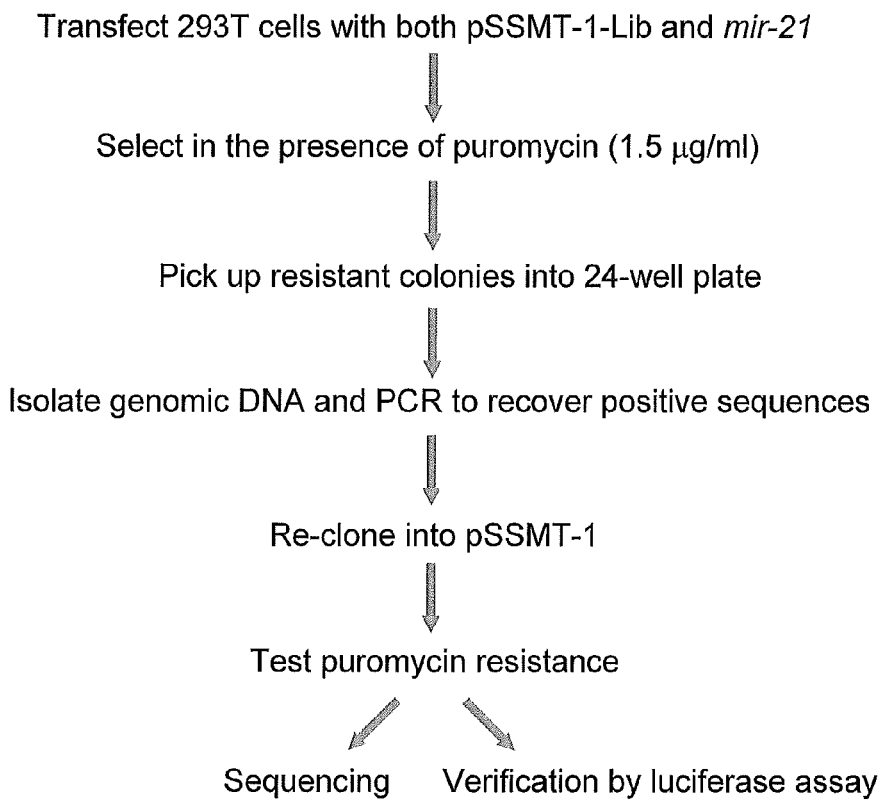
FIG. 5 selection procedure

Schematic description for validation of miR-21 target TPM1 by the selection system.

Validation of miR-21 target TPM1 by the selection system.

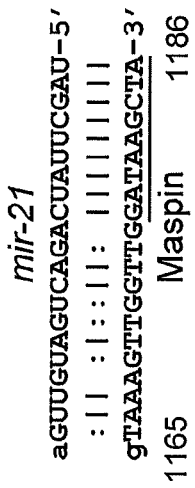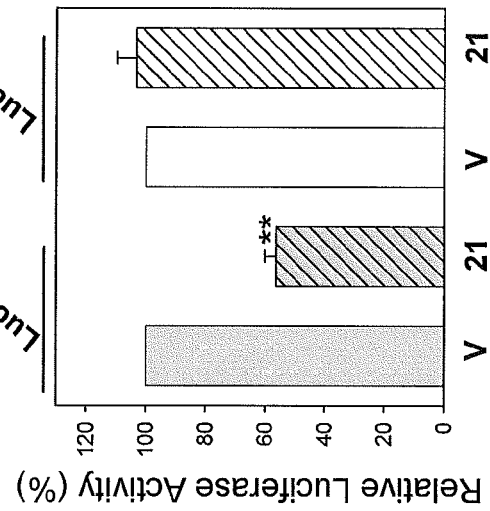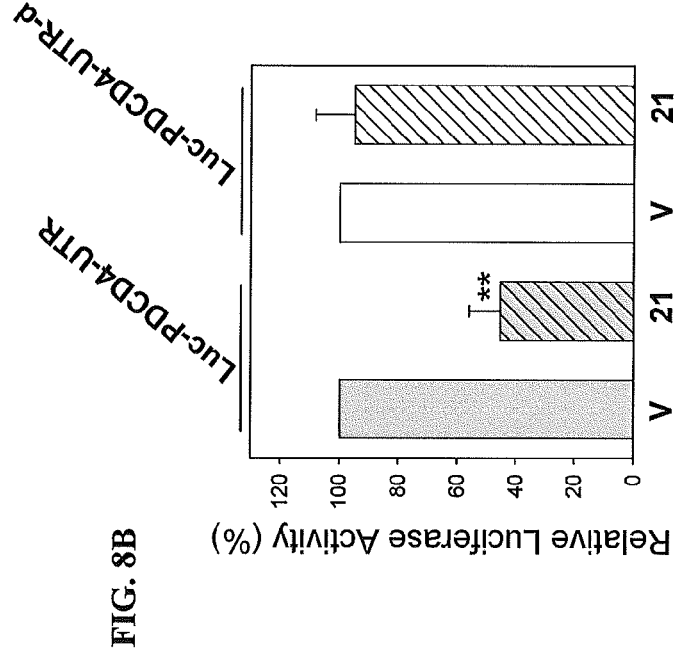
FIG. 8A  FIG. 8C  FIG. 8B  FIG. 8D
Both PDCD4 and maspin are the direct targets for miR-21.

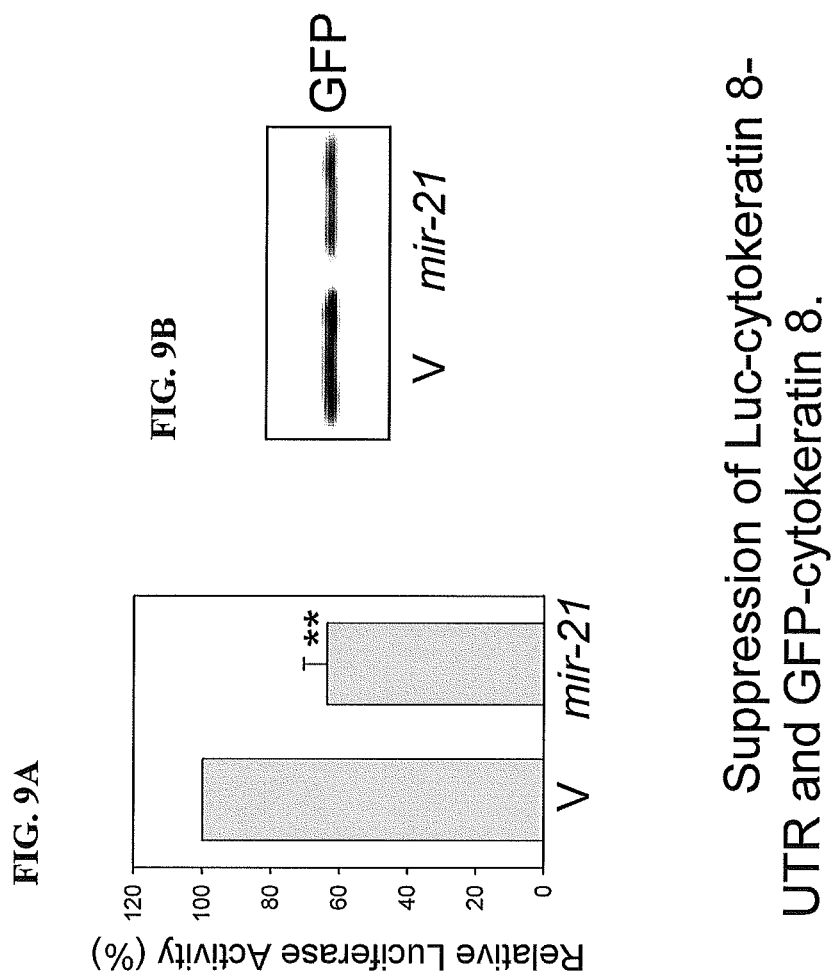

Negative correlation between miR-21 and PDCD4 in the matched breast tumor specimens, as detected by real-time RT-PCR.

Negative correlation between miR-21 and PDCD4 in the matched breast tumor specimens, as detected by immunohistochemistry (IHC) and in situ hybridization (ISH).

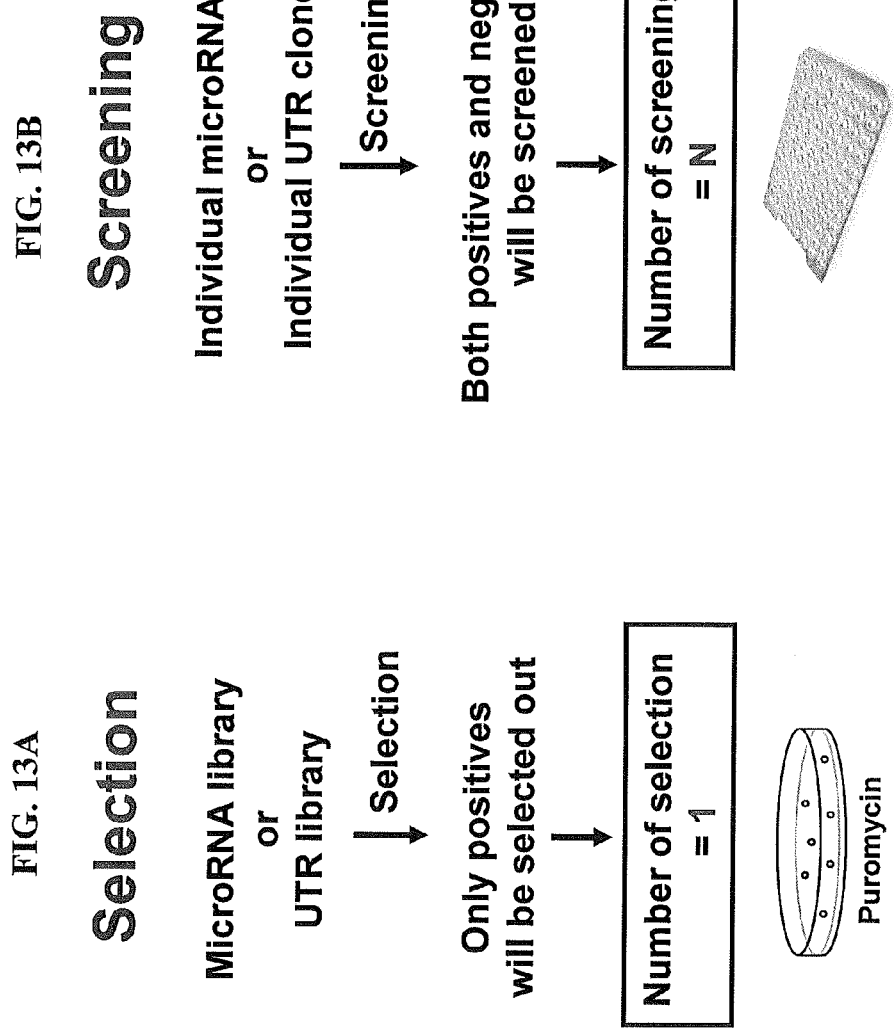

FIG. 14A

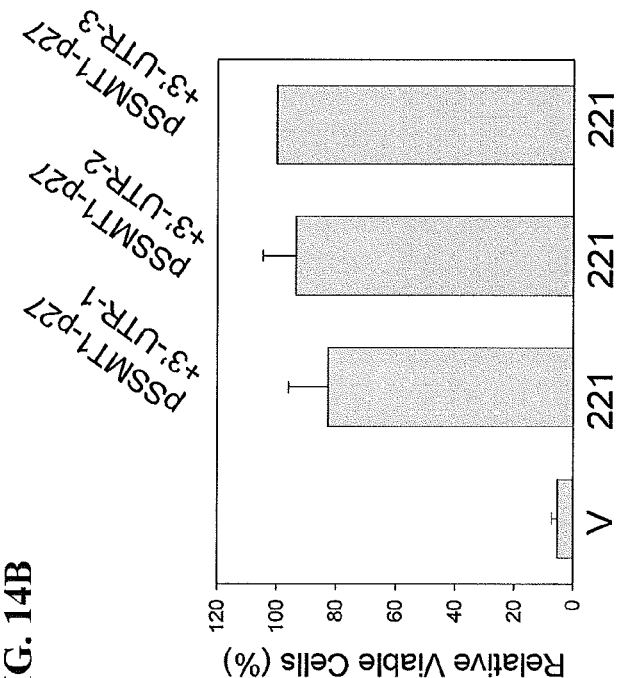

FIG. 14B

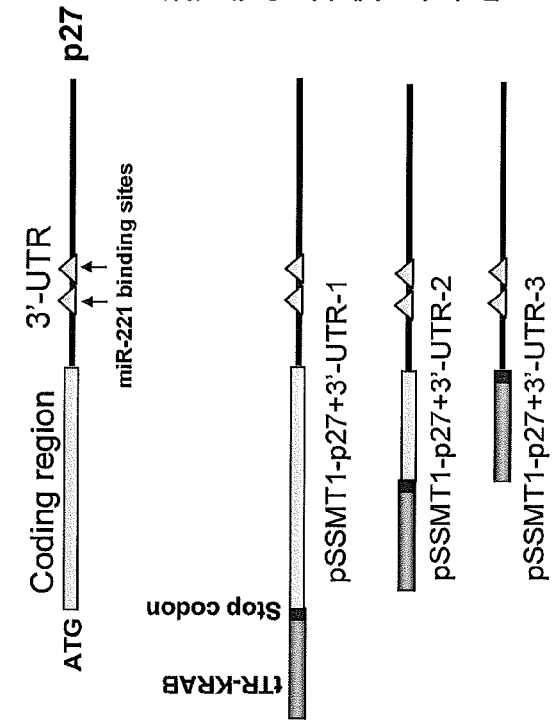

Effect of different regions of p27 on cell survival in our selection system. A, Schematic description of constructs. B, 293T cells were first transfected with indicated selection plasmids along with vector control (V) or miR-221 (221) and then selected in the presence of puromycin (1.0 μg/ml). Relative survival rate by day 5 after selection was calculated by first comparing between vector and miR-221 for each construct and then comparing the value to pSSMT1-p27+3'-UTR-3 (100%). Date are averages of triplicates from the same experiments.

FIG. 15A

Table 1 Summary of putative *mir-21* targets*

| Clone | Name | Access Number |
|---|---|---|
| 1 | Programmed cell death 4 (PDCD4) | NM_014456 |
| 2 | Maspin | NM_002639 |
| 3 | Cytokeratin 8 (KRT8) | NM_002273 |
| 4 | Transmembrane protein 98 (TMEM98) | NM_001033504 |
| 5 | Ribosomal protein L3 (RPL3) | NM_000967 |
| 6 | Fission 1 (mitochondrial outer membrane) | NM_016068 |
| 7 | Guanine nucleotide binding protein (G protein), beta polypeptide 2-like 1 (GNB2L1) | NM_006098 |
| 8 | Small nuclear ribonucleoprotein polypeptide A (SNRPA) | NM_004596 |
| 9 | Ribosomal protein S11(RPS11) | NM_001015 |
| 10 | Ribosomal protein L18a (RPL18A) | NM_000980 |
| 11 | Phosphatidylinositol 3,4,5-trisphosphate-dependent RAC exchanger 1 (PREX1) | NM_020820 |
| 12 | KIAA0841 | XM_945890 |
| 13 | Pyrroline-5-carboxylate reductase 1 (PYCR1) | NM_006907 |
| 14 | Rogdi homolog (Drosophila) (ROGDI) | NM_024589 |

* these clones revealed at least 30% reduction of luciferase activity by *mir-21* compared to vector control, in addition to resistance to puromycin.

Table 2 Genes for target validation

| 1.Tumor promoting genes | Accession # | 3'-UTR (bp) |
|---|---|---|
| HER2/neu, | NM_004448 | 618 |
| ERα, | NM_000125 | 4208 |
| k-Ras, | NM_033360 | 4685 |
| Myc, | NM_002467 | 488 |
| CCND1, | NM_053056 | 3207 |
| bcl-2 | NM_000633 | 5279 |
| Ubc9 | NM_003345 | 596 |
| 2.Tumor suppressors | | |
| p27, | NM_004064 | 1360 |
| RB, | NM_000321 | 1819 |
| pdcd4 | NM_014456 | 1938 |
| 3.Resistance-related genes | | |
| DHFR, bcl-2, CCND1 and Ubc9 | NM_000791 | 2876 |

FIG. 15B

SEQUENCE LISTING

<160> NUMBER OF SEQ ID NOS: 10

<210> SEQ ID NO 1
<211> LENGTH: 28
<212> TYPE: DNA
<213> ORGANISM: Artificial
<220> FEATURE:
<223> OTHER INFORMATION: synthetic sequence

<400> SEQUENCE: 1
cttgggattt gaataggaac ctgcaggt                                28

<210> SEQ ID NO 2
<211> LENGTH: 36
<212> TYPE: DNA
<213> ORGANISM: Artificial
<220> FEATURE:
<223> OTHER INFORMATION: synthetic sequence

<400> SEQUENCE: 2
agctacctgc aggttcctat tcaaatccca aggtac                       36

<210> SEQ ID NO 3
<211> LENGTH: 50
<212> TYPE: DNA
<213> ORGANISM: Artificial
<220> FEATURE:
<223> OTHER INFORMATION: synthetic sequence

<400> SEQUENCE: 3
aggcgtatca cgaggccctt tcgagatcta gtttaccact ccctatcagt        50

<210> SEQ ID NO 4
<211> LENGTH: 21
<212> TYPE: DNA
<213> ORGANISM: Artificial
<220> FEATURE:
<223> OTHER INFORMATION: synthetic sequence

<400> SEQUENCE: 4
ttactagtgc ggaggctgga t                                       21

<210> SEQ ID NO 5
<211> LENGTH: 22
<212> TYPE: DNA
<213> ORGANISM: Artificial
<220> FEATURE:
<223> OTHER INFORMATION: synthetic sequence

<400> SEQUENCE: 5
ttcagagact gcatttgaaa tc                                      22

<210> SEQ ID NO 6
<211> LENGTH: 21
<212> TYPE: DNA
<213> ORGANISM: Artificial
<220> FEATURE:
<223> OTHER INFORMATION: synthetic sequence

<400> SEQUENCE: 6
tgccaagcta cctgcaggtt g                                       21

<210> SEQ ID NO 7
<211> LENGTH: 17
<212> TYPE: RNA
<213> ORGANISM: Artificial

```
<220> FEATURE:
<223> OTHER INFORMATION: synthetic sequence

<400> SEQUENCE: 7
uagcuuauca gacugau                                                          17

<210> SEQ ID NO 8
<211> LENGTH: 22
<212> TYPE: DNA
<213> ORGANISM: Artificial
<220> FEATURE:
<223> OTHER INFORMATION: synthetic sequence

<400> SEQUENCE: 8
agtggaatat tctaataagc ta                                                    22

<210> SEQ ID NO 9
<211> LENGTH: 22
<212> TYPE: RNA
<213> ORGANISM: Artificial sequence
<220> FEATURE:
<223> OTHER INFORMATION: synthetic sequence

<400> SEQUENCE: 9
uagcuuauca gacugauguu ga                                                    22

<210> SEQ ID NO 10
<211> LENGTH: 22
<212> TYPE: DNA
<213> ORGANISM: Artificial sequence
<220> FEATURE:
<223> OTHER INFORMATION: synthetic sequence

<400> SEQUENCE: 10
gtaaagttgg ttggataagc ta                                                    22
```

GENETIC SELECTION SYSTEM FOR IDENTIFICATION OF MICRORNA TARGET GENES

CROSS-REFERENCE TO RELATED APPLICATIONS

This application is a nonprovisional of and claims priority to U.S. Provisional Application Ser. No. 61/000,336, filed Oct. 25, 2007, which document is hereby incorporated by reference to the extent permitted by law.

STATEMENT OF GOVERNMENT SUPPORT

This invention was made with government support under grant number W81XWH-06-1-0604 and grant number W81XWH-08-1-0658 awarded by the U.S. Army Medical Research Acquisition Activity. The government has certain rights in this invention.

BACKGROUND OF THE INVENTION

The present invention generally relates to an expression cassette comprising a 3'-UTR cDNA library fragment, mammalian cells transfected with the expression cassette, and kits comprising the same. Furthermore, methods for identifying target genes for microRNAs are provided that utilize the expression cassette hereof.

MicroRNAs are a class of naturally-occurring small non-coding RNAs that control gene expression by translational repression or mRNA degradation (1-3). They are abundantly expressed and could comprise 1-5% of animal genes (4). Since the discovery of lin-4 and let-7 in Caenorhabditis elegans (5-7), over six thousand microRNAs have been identified in a variety of organisms, including plants, flies and animals through the genomics and bioinformatics effort (8). Like protein-coding genes, microRNAs are transcribed as long primary transcripts (pri-microRNAs) in the nucleus. However, distinct from protein-coding genes, they are subsequently cleaved to produce stem loop structured precursor molecules (pre-microRNAs) of 70-100 nucleotides (nt) in length by the nuclear RNase III enzyme Drosha (9). The pre-microRNAs are then exported to the cytoplasm by exportin-5 (10) where the RNase III enzyme Dicer further processes them into mature microRNAs (~22 nt). One strand of the microRNA duplex is subsequently incorporated into the RNA-induced silencing complex (RISC) that mediates target gene expression. Although the microRNA pathways leading to gene silencing are not fully understood yet, evidence indicates that they target mRNAs for translational repression or mRNA cleavage (11, 12). Since microRNAs are able to silence gene expression by binding to the 3'-untranslated region (3'-UTR) of the gene with partial sequence homology, a single microRNA usually has multiple targets (13). Thus, microRNAs could regulate a large fraction of protein-coding genes. Indeed, as high as 30% of all genes could be microRNA targets (11, 14). In essence, microRNAs can be considered to be modulators of gene regulators and they can cooperate with transcription factors. Together, microRNAs and transcription factors determine gene expression patterns in the cell (15). Therefore, the discovery of microRNAs adds a new layer of gene regulation to the complex gene expression network.

Given the important role of microRNA in regulating cellular pathways, it has been found that a unique set of microRNAs (or microRNA signatures) are often associated with human cancer. Lu et al. reported a general downregulation of a number of microRNAs in tumors compared with normal tissues in multiple human cancers (16). Of considerable interest, microRNA expression profiles are able to successfully classify poorly differentiated tumors whereas mRNA profiles are highly inaccurate for the same samples (16). MicroRNA signatures have also been reported in other types of cancers, including chronic lymphocytic leukemia (CLL) (17), lung cancer (18), pituitary adenomas (19), uterine leiomyomas (20) and adult acute myeloid leukemia (AML) (21). In lung cancer, microRNA expression profiles correlate with survival of lung adenocarcinomas, including those classified as disease stage I; high miR-155 and low let-7a-2 expression correlates with poor survival (18). Hierarchical clustering analysis of microRNA expression profiles is able to distinguish tumor from normal pancreas, pancreatitis and cell lines (22). In pituitary adenomas, 30 microRNAs are differentially expressed between normal pituitary and pituitary adenomas and among them, 24 microRNAs can serve as a predictive signature of pituitary adenoma and 29 microRNAs are able to predict pituitary adenoma histotype (19). In human uterine leiomyomas, 31 of 206 microRNAs examined reveal a distinct microRNA expression profile associated with tumor size and race (20). More interestingly, a solid cancer microRNA signature is suggested by a large portion of overexpressed microRNAs from a large-scale miRnome analysis on 540 samples, including lung, breast, stomach, prostate, colon, and pancreatic tumors (23). Together, these findings highlight the potential of microRNA profiling in cancer diagnosis (16).

The fundamental role of microRNAs in regulating cellular pathways suggests that deregulation of microRNAs affects normal cell growth and development, leading to a variety of disorders including neurological diseases (24) and human cancer (12, 25-28). Specific overexpression or underexpression has been shown to correlate with particular tumor types (16, 17, 32-34) because overexpression of a particular set of microRNAs could result in down-regulation of tumor suppressor genes, whereas their underexpression could lead to oncogene up-regulation, suggesting that microRNAs may function as either oncogenes or tumor suppressor genes (29). Since microRNAs are often located at fragile sites or in repetitive genomic sequences of chromosomal regions (30), this may explain why microRNA expression deregulation occurs frequently in human cancer. For instance, 68% of investigated patients suffering from B-cell chronic lymphocytic leukemia (CLL) have been shown to have a deletion located at chromosome 13q14 where the miR-15 and miR-16 genes reside and are under-represented in many B-CLL patients (31).

Apparently, whether a microRNA functions as an oncogene or tumor suppressor is largely determined by the target genes of each particular microRNA. For example, tumor suppressive microRNAs, such as let-7, miR-15 and miR-16, are able to suppress expression of oncogenes. let-7 suppresses ras oncogene and is downregulated in lung cancer (32); miR-15 and miR-16 suppress Bcl-2 anti-apoptotic gene, and they are deleted or downregulated in leukemia (31, 33). In contrast, oncogenic microRNAs can silence tumor suppressor genes. miR-17-5p and miR-20a control the balance of cell death and proliferation driven by the proto-oncogene c-Myc (34) and miR-17-5p serves as an oncogene in lymphoma and lung cancer (35, 36). Similarly, a cluster consisting of miR-372 and miR-373 have been shown to function as oncogenes in testicular germ cell tumors by suppressing the p53 pathway (37). Moreover, it has been demonstrated by the present inventors and others that antisense miR-21 oligonucleotide suppresses tumor cell growth which is associated with increased apoptosis and decreased cell proliferation (38, 39)

thereby suggesting that miR-21 is an oncogene. The present inventors and others subsequently identified the tumor suppressor gene tropomyosin 1 (TPM1) as a direct miR-21 target gene (40). Furthermore, miR-21 also plays a role in cell invasion and tumor metastasis, which is likely through regulation of multiple miR-21 target genes, such as TPM1, programmed cell death 4 (pdcd4) and maspin (41). Of interest, certain microRNAs may specifically modulate only tumor metastasis. For example, miR-10b functions as a metastasis initiation factor and overexpression of miR-10b causes breast tumor invasion and metastasis, but it has no effect on primary tumor growth (42). On the other hand, miR-335 suppresses metastasis and migration through targeting of the progenitor cell transcription factor SOX4 and extracellular matrix component tenascin C (43).

Since microRNAs regulate cellular pathways by suppression of their specific target genes, identification of microRNA target genes is critical to the understanding of molecular mechanisms of microRNA-mediated tumorigenesis. Computational algorithms have been a major driving force in predicting microRNA targets (44-46). The approaches are mainly based on base pairing between microRNA and target gene 3'-UTR, emphasizing the location of microRNA complementary elements in 3'-UTR of target mRNAs, the concentration in the seed sequence (6-8 bp) of continuous Watson-Crick base pairing in 5' proximal half of the microRNA and the phylogenetic conservation of the complementary sequences in 3'-UTRs of orthologous genes. They provide very useful primary sources in search for microRNA targets. However, despite the fundamentally similar approaches used for the published screens for microRNA targets, predicted targets for a given microRNA often vary among different methods. Presumably the approaches differ in certain important details, such as defining phylogenetic conservation, thermodynamic and statistical factors applied to score and rank predicted sites. The fact that mature microRNAs are short and typically contain several sequence mismatches with their target transcripts has complicated computational target predictions. This might explain why computer-aided algorithms are still unable to provide a precise picture of microRNA regulatory networks. In addition, a recent report indicates that perfect seed pairing is not a generally reliable predictor for miRNA-target interactions at least in some cases (47, 48), which further highlights the difficulty of microRNA target predictions. Thus, they can only serve a complementary approach and certainly need in vivo experimental validations. Another challenge is that it is not clear whether a microRNA can target mRNA which does not carry a putative binding site for this microRNA. If this is the case, such a target gene may escape from these prediction methods because all of them are mainly based on sequence homology between microRNA and mRNA. More recently, there are reports that microRNAs are able to bind to 5'-UTR or coding regions and silence or even enhance the corresponding genes. These findings suggest that microRNAs are not necessarily restricted to the 3'-UTR to exert their function. However, the currently prediction methods are mainly based on the 3'-UTR. In other words, some microRNA targets would also escape from these prediction methods.

Regarding microRNA prediction methods, currently there is no clear consensus as to which one is most reliable. The present inventors have compared four commonly cited microRNA target prediction programs, TargetScan4 (49), miRBase Target5 (http://microrna.sanger.ac.uk/targets/v5/), PicTar (50) and miRanda (http://www.microma.org) (51). In general, miRBase Target5 and miRanda tend to predict more targets than TargetScan4 or PicTar does presumably because the first two programs do not weigh as much on conservations among different species as the other two programs. Using miR-21 as an example, miRBase Target5 and miRanda predict 1000 and 2501 targets, respectively. On the other hand, TargetScan4 and PicTar predict 186 and 175 targets, respectively. However, only a small fraction of predicted targets among these methods overlap thereby suggesting that each method has its own unique set of parameters. For example, some of these models have recently been refined to consider the presence of secondary structures and other features of the 3'-UTR sequence surrounding the target site, and for the ability of complementarity at the 3' end of the cognate miRNA to compensate for imperfect seed matching (49, 52). Nevertheless, despite these efforts, little is known about the prediction accuracy of these methods because only a very limited number of targets have been experimentally validated. Therefore, there is a need in the art for systematic target validation methods.

Microarray technology could be one of target validation approaches because it is capable of determining expression of potential microRNA targets at the mRNA level (53, 54). However, given that a large fraction of microRNA target genes are silenced by the translation repression mechanism, those microRNA targets may escape from the microarray detection. Alternatively, microRNAs can be used as endogenous cytoplasmic primers to synthesize cDNA on an mRNA template (55) such that recovered primers would presumably be functional microRNAs. However, this is technically challenging because of limited sequence homology between mRNA and microRNA. In addition, it could be extremely difficulty to recover those microRNAs that can cause mRNA degradation. Alternatively, biochemical or proteomic methods have been used for this purpose (56-61), but they could be labor intensive.

Currently, in research laboratories a common approach to validate whether a gene is a direct microRNA target involves cloning of the 3'-UTR of this gene into a reporter (e.g., luciferase), followed by reporter assays. It is further verified to be suppressed by a given microRNA at the mRNA level (e.g., real-time RT-PCR) or at the protein level (e.g., Western blot). Apparently, validation of multiple microRNA targets with this approach needs a high throughput screening system because each microRNA will have to be individually tested against a given UTR sequence, which requires intensive labor and costly reagents (FIG. 13 right). Therefore, the selection system described here will save tremendous time and cost because this method allows selection of positive microRNA/mRNA interactions (FIG. 13 left).

The genetic selection method of the present invention represents a unique systematic validation system for microRNA targets that provides a comprehensive picture of microRNA/mRNA interactions for a given gene or a given microRNA. One of the advantages of this system is that it allows for the determination of microRNA/mRNA interactions whether mRNA degradation or translation repression is involved or whether conserved microRNA binding sites are required. Moreover, this is a simple but powerful selection method that does not require intensive labor or costly instrument and reagents and it is suitable for a large number of microRNAs or target genes.

The following references that are referred throughout this disclosure are hereby incorporated by reference in their entirety to the extent permitted by law. These references merely serve to support the invention and to provide background and context. Applicant reserves the right to challenge the veracity of any statements therein made.

1. Pillai R S MicroRNA function: multiple mechanisms for a tiny RNA? Rna 2005; 11:1753-1761.
2. Zamore P D, Haley B Ribo-gnome: the big world of small RNAs. Science 2005; 309:1519-1524.
3. Bartel D P MicroRNAs: genomics, biogenesis, mechanism, and function. Cell 2004; 116:281-297.
4. Berezikov E, Guryev V, van de Belt J, Wienholds E, Plasterk R H, Cuppen E Phylogenetic shadowing and computational identification of human microRNA genes. Cell 2005; 120:21-24.
5. Lee R C, Feinbaum R L, Ambros V The C. elegans heterochronic gene lin-4 encodes small RNAs with antisense complementarity to lin-14. Cell 1993; 75:843-854.
6. Wightman B, Ha I, Ruvkun G Posttranscriptional regulation of the heterochronic gene lin-14 by lin-4 mediates temporal pattern formation in C. elegans. Cell 1993; 75:855-862.
7. Reinhart B J. Slack F J. Basson M. Pasquinelli A E. Bettinger J C. Rougvie A E, et al. The 21-nucleotide let-7 RNA regulates developmental timing in Caenorhabditis elegans. Nature 2000; 403:901-906.
8. Griffiths-Jones S, Saini H K, van Dongen S, Enright A J miRBase: tools for microRNA genomics. Nucleic Acids Res 2008; 36:D154-158.
9. Kim V N MicroRNA biogenesis: coordinated cropping and dicing. Nat Rev Mol Cell Biol 2005; 6:376-385.
10. Yi R, Qin Y, Macara I G, Cullen B R Exportin-5 mediates the nuclear export of pre-microRNAs and short hairpin RNAs. Genes Dev 2003; 17:3011-3016.
11. Du T, Zamore PD microPrimer: the biogenesis and function of microRNA. Development 2005; 132:4645-4652.
12. Esquela-Kerscher A, Slack F J OncomiRs—microRNAs with a role in cancer. Nat Rev Cancer 2006; 6:259-269.
13. Brennecke J, Stark A, Russell R B, Cohen S M Principles of microRNA-target recognition. PLoS Biol 2005; 3:e85.
14. Lewis B P, Burge C B, Bartel D P Conserved seed pairing, often flanked by adenosines, indicates that thousands of human genes are microRNA targets. Cell 2005; 120:15-20.
15. Hobert O Gene regulation by transcription factors and microRNAs. Science 2008; 319:1785-1786.
16. Lu J. Getz G. Miska E A. Alvarez-Saavedra E. Lamb J. Peck D, et al. MicroRNA expression profiles classify human cancers. Nature 2005; 435:834-838.
17. Calin G A. Ferracin M. Cimmino A. Di Leva G. Shimizu M. Wojcik S E, et al. A MicroRNA signature associated with prognosis and progression in chronic lymphocytic leukemia. N Engl J Med 2005; 353:1793-1801.
18. Yanaihara N. Caplen N. Bowman E. Seike M. Kumamoto K. Yi M, et al. Unique microRNA molecular profiles in lung cancer diagnosis and prognosis. Cancer Cell 2006; 9:189-198.
19. Bottoni A. Zatelli M C. Ferracin M. Tagliati F. Piccin D. Vignali C, et al. Identification of differentially expressed microRNAs by microarray: a possible role for microRNA genes in pituitary adenomas. J Cell Physiol 2007; 210:370-377.
20. Wang T. Zhang X. Obijuru L. Laser J. Aris V. Lee P, et al. A micro-RNA signature associated with race, tumor size, and target gene activity in human uterine leiomyomas. Genes Chromosomes Cancer 2007; 46:336-347.
21. Debernardi S, Skoulakis S, Molloy G, Chaplin T, Dixon-McIver A, Young B D MicroRNA miR-181a correlates with morphological sub-class of acute myeloid leukaemia and the expression of its target genes in global genome-wide analysis. Leukemia 2007.
22. Lee E J. Gusev Y. Jiang J. Nuovo G J. Lerner M R. Frankel W L, et al. Expression profiling identifies microRNA signature in pancreatic cancer. Int J Cancer 2007; 120:1046-1054.
23. Volinia S. Calin G A. Liu C G. Ambs S. Cimmino A. Petrocca F, et al. A microRNA expression signature of human solid tumors defines cancer gene targets. Proc Natl Acad Sci USA 2006; 103:2257-2261.
24. Dostie J, Mourelatos Z, Yang M, Sharma A, Dreyfuss G Numerous microRNPs in neuronal cells containing novel microRNAs. Rna 2003; 9:180-186.
25. Hwang H W, Mendell J T MicroRNAs in cell proliferation, cell death, and tumorigenesis. Br J Cancer 2006; 94:776-780.
26. Croce C M, Calin G A miRNAs, cancer, and stem cell division. Cell 2005; 122:6-7.
27. Hammond S M MicroRNAs as oncogenes. Curr Opin Genet Dev 2006; 16:4-9.
28. Gregory R I, Shiekhattar R MicroRNA biogenesis and cancer. Cancer Res 2005; 65:3509-3512.
29. Chen C Z MicroRNAs as oncogenes and tumor suppressors. N Engl J Med 2005; 353:1768-1771.
30. Calin G A. Liu C G. Sevignani C. Ferracin M. Felli N. Dumitru C D, et al. MicroRNA profiling reveals distinct signatures in B cell chronic lymphocytic leukemias. Proc Natl Acad Sci USA 2004; 101:11755-11760.
31. Calin G A. Dumitru C D. Shimizu M. Bichi R. Zupo S. Noch E, et al. Frequent deletions and down-regulation of micro-RNA genes miR15 and miR16 at 13q14 in chronic lymphocytic leukemia. Proc Natl Acad Sci USA 2002; 99:15524-15529.
32. Johnson S M. Grosshans H. Shingara J. Byrom M. Jarvis R. Cheng A, et al. RAS is regulated by the let-7 microRNA family. Cell 2005; 120:635-647.
33. Cimmino A. Calin G A. Fabbri M. Iorio M V. Ferracin M. Shimizu M, et al. miR-15 and miR-16 induce apoptosis by targeting BCL2. Proc Natl Acad Sci USA 2005; 102:13944-13949.
34. O'Donnell K A, Wentzel E A, Zeller K I, Dang C V, Mendell J T c-Myc-regulated microRNAs modulate E2F1 expression. Nature 2005; 435:839-843.
35. He L. Thomson J M. Hemann M T. Hernando-Monge E. Mu D. Goodson S, et al. A microRNA polycistron as a potential human oncogene. Nature 2005; 435:828-833.
36. Hayashita Y. Osada H. Tatematsu Y. Yamada H. Yanagisawa K. Tomida S, et al. A polycistronic microRNA cluster, miR-17-92, is overexpressed in human lung cancers and enhances cell proliferation. Cancer Res 2005; 65:9628-9632.
37. Voorhoeve P M. le Sage C. Schrier M. Gillis A J. Stoop H. Nagel R, et al. A genetic screen implicates miRNA-372 and miRNA-373 as oncogenes in testicular germ cell tumors. Cell 2006; 124:1169-1181.
38. Si M L, Zhu S, Wu H, Lu Z, Wu F, Mo Y Y miR-21-mediated tumor growth. Oncogene 2007; 26:2799-2803.
39. Chan J A, Krichevsky A M, Kosik K S MicroRNA-21 is an antiapoptotic factor in human glioblastoma cells. Cancer Res 2005; 65:6029-6033.
40. Zhu S, Si M L, Wu H, Mo Y Y MicroRNA-21 targets the tumor suppressor gene tropomyosin 1 (TPM1). J Biol Chem 2007.
41. Zhu S, Wu H, Wu F, Nie D, Sheng S, Mo Y Y MicroRNA-21 targets tumor suppressor genes in invasion and metastasis. Cell Res 2008; 18:350-359.
42. Ma L, Teruya-Feldstein J, Weinberg R A Tumour invasion and metastasis initiated by microRNA-10b in breast cancer. Nature 2007; 449:682-688.

43. Tavazoie S F. Alarcon C. Oskarsson T. Padua D. Wang Q. Bos PD, et al. Endogenous human microRNAs that suppress breast cancer metastasis. Nature 2008; 451:147-152.

44. Stark A, Brennecke J, Russell R B, Cohen S M Identification of Drosophila MicroRNA targets. PLoS Biol 2003; 1:E60.

45. Lewis B P, Shih I H, Jones-Rhoades M W, Bartel D P, Burge C B Prediction of mammalian microRNA targets. Cell 2003; 115:787-798.

46. Kiriakidou M, Nelson P T, Kouranov A, Fitziev P, Bouyioukos C, Mourelatos Z, et al. A combined computational-experimental approach predicts human microRNA targets. Genes Dev 2004; 18:1165-1178.

47. Didiano D, Hobert 0 Perfect seed pairing is not a generally reliable predictor for miRNA-target interactions. Nat Struct Mol Biol 2006; 13:849-851.

48. Didiano D, Hobert O Molecular architecture of a miRNA-regulated 3' UTR. Rna 2008.

49. Grimson A, Farh K K, Johnston W K, Garrett-Engele P, Lim L P, Bartel D P MicroRNA targeting specificity in mammals: determinants beyond seed pairing. Mol Cell 2007; 27:91-105.

50. Krek A. Grun D. Poy M N. Wolf R. Rosenberg L. Epstein E J, et al. Combinatorial microRNA target predictions. Nat Genet 2005; 37:495-500.

51. John B, Enright A J, Aravin A, Tuschl T, Sander C, Marks D S Human MicroRNA targets. PLoS Biol 2004; 2:e363.

52. Long D, Lee R, Williams P, Chan C Y, Ambros V, Ding Y Potent effect of target structure on microRNA function. Nat Struct Mol Biol 2007; 14:287-294.

53. Huang J C. Babak T. Corson T W. Chua G. Khan S. Gallie B L, et al. Using expression profiling data to identify human microRNA targets. Nat Methods 2007; 4:1045-1049.

54. Lim L P. Lau N C. Garrett-Engele P. Grimson A. Schelter J M. Castle J, et al. Microarray analysis shows that some microRNAs downregulate large numbers of target mRNAs. Nature 2005; 433:769-773.

55. Vatolin S, Navaratne K, Weil R J A novel method to detect functional microRNA targets. J Mol Biol 2006; 358: 983-996.

56. Karginov F V, Conaco C, Xuan Z, Schmidt B H, Parker J S, Mandel G, et al. A biochemical approach to identifying microRNA targets. Proc Natl Acad Sci USA 2007; 104: 19291-19296.

57. Zhu S, Si M L, Wu H, Mo Y Y MicroRNA-21 Targets the Tumor Suppressor Gene Tropomyosin 1 (TPM1). J Biol Chem 2007; 282:14328-14336.

58. Easow G, Teleman A A, Cohen S M Isolation of microRNA targets by miRNP immunopurification. Rna 2007; 13:1198-1204.

59. Beitzinger M, Peters L, Zhu J Y, Kremmer E, Meister G Identification of human microRNA targets from isolated argonaute protein complexes. RNA Biol 2007; 4:76-84.

60. Zhang L. Ding L. Cheung T H. Dong M Q. Chen J. Sewell A K, et al. Systematic identification of C. elegans miRISC proteins, miRNAs, and mRNA targets by their interactions with GW182 proteins AIN-1 and AIN-2. Mol Cell 2007; 28:598-613.

61. Hendrickson D G, Hogan D J, Herschlag D, Ferrell J E, Brown P O Systematic identification of mRNAs recruited to argonaute 2 by specific microRNAs and corresponding changes in transcript abundance. PLoS ONE 2008; 3:e2126.

62. Mo Y Y, Wang C, Beck W T A novel nuclear localization signal in human DNA topoisomerase I. J Biol Chem 2000; 275:41107-41113.

63. Wu F, Chiocca S, Beck W T, Mo Y Y Gam 1-associated alterations of drug responsiveness through activation of apoptosis. Mol Cancer Ther 2007; 6:1823-1830.

64. Margolin J F, Friedman J R, Meyer W K, Vissing H, Thiesen H J, Rauscher F J, 3rd Kruppel-associated boxes are potent transcriptional repression domains. Proc Natl Acad Sci USA 1994; 91:4509-4513.

65. Deuschle U, Meyer W K, Thiesen H J Tetracycline-reversible silencing of eukaryotic promoters. Mol Cell Biol 1995; 15:1907-1914.

66. Herchenroder O, Hahne J C, Meyer W I, Thiesen H J, Schneider J Repression of the human immunodeficiency virus type 1 promoter by the human KRAB domain results in inhibition of virus production. Biochim Biophys Acta 1999; 1445:216-223.

67. Rittner K, Schultz H, Pavirani A, Mehtali M Conditional repression of the E2 transcription unit in E1-E3-deleted adenovirus vectors is correlated with a strong reduction in viral DNA replication and late gene expression in vitro. J Virol 1997; 71:3307-3311.

68. Cmarik J L. Min H. Hegamyer G. Zhan S. Kulesz-Martin M. Yoshinaga H, et al. Differentially expressed protein Pdcd4 inhibits tumor promoter-induced neoplastic transformation. Proc Natl Acad Sci USA 1999; 96:14037-14042.

69. Lau A T, Chiu J F The possible role of cytokeratin 8 in cadmium-induced adaptation and carcinogenesis. Cancer Res 2007; 67:2107-2113.

70. Zhu S W H, Wu F, Nie D, Sheng S, Mo Y Y. MicroRNA-21 targets tumor suppressor genes in invasion and metastasis. Cell Research 2007; In press.

71. Stark A, Brennecke J, Bushati N, Russell R B, Cohen S M Animal MicroRNAs confer robustness to gene expression and have a significant impact on 3'UTR evolution. Cell 2005; 123:1133-1146.

72. Ørom U A, Nielsen F C, Lund A H, MicroRNA-10a binds the 5'UTR of ribosomal protein mRNAs and enhances their translation, 1. Mol Cell. 2008 May 23; 30(4):460-71.

73. Forman J J, Legesse-Miller A, Coller H A. A search for conserved sequences in coding regions reveals that the let-7 microRNA targets Dicer within its coding sequence. Proc Natl Acad Sci USA. 2008 Sep. 30; 105(39):14879-84.

74. Tay Y, Zhang J, Thomson A M, Lim B, Rigoutsos I. MicroRNAs to Nanog, Oct4 and Sox2 coding regions modulate embryonic stem cell differentiation. Nature. 2008 September 17.

75. Baek D, Villen J, Shin C, Camargo F D, Gygi S P, Bartel D P, The impact of microRNAs on protein output, Nature. 2008 Sep. 4; 455(7209):64-71 Epub 2008 July 30.

76. Selbach M, Schwanhausser B, Thierfelder N, Fang Z, Khanin R, Rajewsky N., Widespread changes in protein synthesis induced by microRNAs, Nature. 2008 Sep. 4; 455 (7209):58-63. Epub 2008 July 30.

77. Zhu S, Wu H, Wu F, Nie D, Sheng S, Mo Y Y. MicroRNA-21 targets tumor suppressor genes in invasion and metastasis. Cell Res. 2008 March; 18(3):350-9.

SUMMARY OF THE INVENTION

In one of many illustrative, non-limiting aspects of the present invention, there is provided an expression cassette comprising a 3'-UTR cDNA library fragment, mammalian cells transfected with the expression cassette, and kits comprising the same. Furthermore, methods for identifying target genes for microRNAs are provided that utilize the expression cassette hereof. The following abbreviations and terms are used throughout the specification and have the following definitions:

When introducing elements of the present invention or embodiments(s) thereof, the articles "a", "an", "the" and "said" are intended to mean that there are one or more of the elements. The terms "comprising", "including" and "having" are intended to be open and inclusive and mean that there may be additional elements other than the listed elements.

A "bp" is an abbreviation for base pair.

A "ds" is an abbreviation for double-stranded.

A "GFP" is an abbreviation for green fluorescent protein.

An "nt" is an abbreviation for nucleotide.

A "target gene" refers to any gene suitable for regulation of expression, including both endogenous chromosomal genes and transgenes, as well as episomal or extrachromosomal genes, mitochondrial genes, chloroplastic genes, viral genes, bacterial genes, animal genes, plant genes, protozoal genes and fungal genes.

A "library" as used herein refers to a collection of nucleic acid sequences that possesses a common characteristic. For example, a library of nucleic acids can be representative of all possible configurations of a nucleic acid sequence over a defined length. Alternatively, a nucleic acid library may be a collection of sequences that represents a particular subset of the possible sequence configurations of a nucleic acid of a defined length. A library may also represent all or part of the genetic information of a particular organism. A nucleic acid "library" is typically, but not necessarily, cloned into a vector.

The term "gene" refers to a nucleic acid (e.g., DNA) sequence that comprises coding sequences necessary for the production of a polypeptide or precursor or RNA (e.g., tRNA, siRNA, rRNA, etc.). The polypeptide can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the sequences located adjacent to the coding region on both the 5' and 3' ends, such that the gene corresponds to the length of the full-length mRNA. The sequences that are located 5' of the coding region and which are present on the mRNA are referred to as 5' untranslated sequences. The sequences that are located 3' or downstream of the coding region and that are present on the mRNA are referred to as 3' untranslated sequences. The term "gene" encompasses both cDNA and genomic forms of a gene. A genomic form or clone of a gene contains the coding region, which may be interrupted with non-coding sequences termed "introns" or "intervening regions" or "intervening sequences." Introns are removed or "spliced out" from the nuclear or primary transcript, and are therefore absent in the messenger RNA (mRNA) transcript. The mRNA functions during translation to specify the sequence or order of amino acids in a nascent polypeptide.

The term "expression vector" refers to both viral and non-viral vectors comprising a nucleic acid expression cassette.

The term "expression cassette" is used to define a nucleotide sequence containing regulatory elements operably linked to a coding sequence that result in the transcription and translation of the coding sequence in a cell.

A "mammalian promoter" refers to a transcriptional promoter that functions in a mammalian cell that is derived from a mammalian cell, or both.

A "mammalian minimal promoter" refers to a 'core' DNA sequence required to properly initiate transcription via RNA polymerase binding, but which exhibits only token transcriptional activity in the absence of any operably linked transcriptional effector sequences.

The phrase "open reading frame" or "coding sequence" refers to a nucleotide sequence that encodes a polypeptide or protein. The coding region is bounded in eukaryotes, on the 5' side by the nucleotide triplet "ATG" that encodes the initiator methionine and on the 3' side by one of the three triplets which specify stop codons (i.e., TAA, TAG, and TGA).

"Operably linked" is defined to mean that the nucleic acids are placed in a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous. However, enhancers do not have to be contiguous. Linking is accomplished by ligation at convenient restriction sites. If such sites do not exist, the synthetic oligonucleotide adaptors or linkers are used in accord with conventional practice.

"Recombinant" refers to the results of methods, reagents, and laboratory manipulations in which nucleic acids or other biological molecules are enzymatically, chemically or biologically cleaved, synthesized, combined, or otherwise manipulated ex vivo to produce desired products in cells or other biological systems. The term "recombinant DNA" refers to a DNA molecule that is comprised of segments of DNA joined together by means of molecular biology techniques.

"Transfection" is the term used to describe the introduction of foreign material such as foreign DNA into eukaryotic cells. It is used interchangeably with "transformation" and "transduction" although the latter term, in its narrower scope refers to the process of introducing DNA into cells by viruses, which act as carriers. Thus, the cells that undergo transfection are referred to as "transfected," "transformed" or "transduced" cells.

The term "plasmid" as used herein, refers to an independently replicating piece of DNA. It is typically circular and double-stranded.

A "reporter gene" refers to any gene the expression of which can be detected or measured using conventional techniques known to those skilled in the art.

Other objects and features will be in part apparent and in part pointed out hereinafter.

BRIEF DESCRIPTION OF THE SEVERAL VIEWS OF THE DRAWING

In the accompanying drawings that form a part of the specification and that are to be read in conjunction therewith:

FIG. 1 is a schematic representation of a plasmid pSSMT1 carrying both tTR-KRAB and tetO-Pu in accordance with one embodiment of the present invention;

FIG. 2 is a schematic representation of the construction of a pSSMT1 library in accordance with one embodiment of the present invention;

FIG. 4 is a schematic representation of primers derived from known sequences flanking the inserts in accordance with one embodiment of the present invention;

FIG. 5 is a schematic representation of the selection system in accordance with one embodiment of the present invention;

FIG. 8A is a representation of a programmed cell death 4 (PDCD4)/miR-21 target in accordance with one embodiment of the present invention;

FIG. 8B is a representation of a maspin/miR-21 target in accordance with one embodiment of the present invention;

FIG. 8C is a graphical representation showing that PDCD4 is a direct target for miR-21 in accordance with one embodiment of the present invention;

FIG. 8D is a graphical representation showing that maspin is a direct target for miR-21 in accordance with one embodiment of the present invention;

FIG. 9A is a graphical representation showing suppression of Luc-cytokeratin 8 UTR by miR-21 in accordance with one embodiment of the present invention;

FIG. 9B is a representation of a gel-electrophoresis analysis showing the downregulation of the GFP protein by miR-21 when the cytokeratin 8 UTR was cloned downstream of GFP in accordance with one embodiment of the present invention;

FIG. 13A is a schematic representation of one embodiment of the selection method of the present invention;

FIG. 13B is a schematic representation of a prior art screening method;

FIG. 14A is a schematic representation of constructs in accordance with one embodiment of the present invention;

FIG. 14B is a graphical representation of the survival rates of the constructs of FIG. 14A in accordance with one embodiment of the present invention;

FIG. 15A is a table summarizing putative mir-21 targets; and

FIG. 15B is a table providing genes for target validation.

DETAILED DESCRIPTION OF THE INVENTION

Figures 3A, 3B:
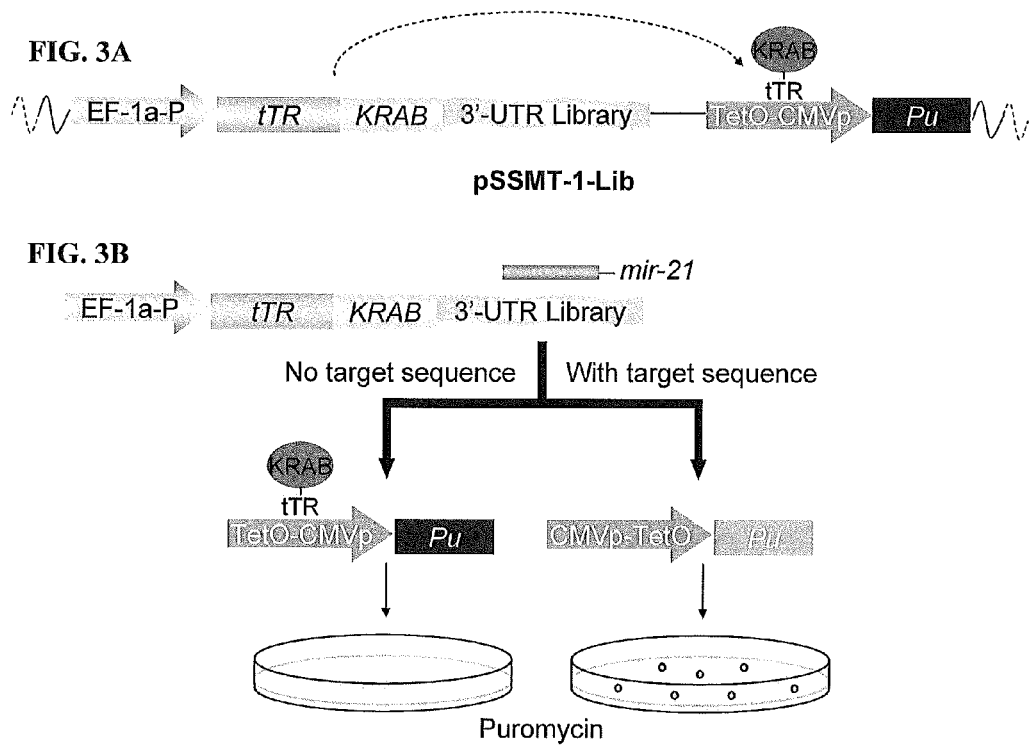
FIG. 3A is a schematic representation of one embodiment of the selection method of the present invention.
FIG. 3B is a schematic representation of another embodiment of the selection method of the present invention.

The present invention is generally directed to a genetic selection system capable of identifying target genes for microRNAs. In particular, there is provided herein an expression cassette including at least one repressor, at least one 3'-UTR cDNA library fragment operably linked to the repressor, an operator gene corresponding to the repressor which is operably linked to a constitutive promotor, and an antibiotic resistance gene operably linked to the constitutive promotor.

As one skilled in the art will appreciate, the expression cassette hereof is expressible in and/or transforms any mammalian cells suitable for use in the present invention. In certain embodiments, a mammalian cell can be a mammalian cell that is isolated from an animal (i.e., a primary cell) or a mammalian cell line. Methods for cell isolation from animals are well known in the art. In some embodiments, a primary cell is isolated from a mouse. In other embodiments, a primary cell is isolated from a human. In still other embodiments, a mammalian cell line can be used. Exemplary cell lines include HEK293 (human embryonic kidney), HT1080 (human fibrosarcoma), NTera2D (human embryonic teratoma), HeLa (human cervical adenocarcinoma), Caco2 (human colon adenocarcinoma), HepG2 (human liver hepatocellular carcinoma), Cos-7 (monkey kidney), ES-D3 (mouse embryonic stem cell), BALBC/3T3 (mouse fibroblast), hES H1 (human embryonic stem cell), MCF-7 and MDA-MB-231 (human breast cancer). Host cell lines are typically available from, for example, the American Tissue Culture Collection (ATCC), any approved Budapest treaty site or other biological depository. In still other embodiments, a mammalian embryonic stem (ES) cell can be used, such as a mouse ES cell mES-D3 or a human ES cell hES H1.

The expression cassette of the present invention may be contained in a plasmid, shuttle vector, viral vector, or the like, and the expression cassette or plasmid hereof may include, in a 5' to 3' direction, at least one repressor, at least one fusion protein, and combinations thereof. To enable the selection method of the present invention, the expression cassette hereof is also configured to be transfected by a microDNA-expressing vector capable of gene suppression. Suitable microDNA include, but are not limited to, miR-21, miR-15, miR-16, miR-17-5p, miR-20a, miR-372, miR-373, miR-335, miR-10b, miR-30, miR-224, and let-7.

Suitable repressors include, but are not limited to, tetracycline repressors (tetR), Lac I, and combinations thereof. Alternatively or in combination, a fusion protein may be used. A fusion protein is derived from a repressor and a repressor domain of a protein. In an illustrative example, a plasmid pSSMT-1 was constructed to carry tTR-KRAB which is a fusion protein derived from tetracycline repressor (tTR) and a repressor domain of the human Kox1 zinc finger protein (64). This fusion protein has been shown to tightly control the target gene expression by binding to the corresponding tetO (65-67). Moreover, tTR-KRAB is able to effectively silence gene expression from tetO sequences placed more than 3 kb from the transcriptional start site (65).

In certain embodiments, the expression cassette of the present invention may also include a 3'-untranslated region (3'-UTR) cDNA library or library fragment operably linked to the repressor, the fusion protein, or a combination thereof. It will be appreciated by one skilled in the art that any 3'-UTR cDNA library or library fragment suitable for use in the present invention may be used including tumor-specific UTR libraries, pathway-specific UTR libraries, and genome-wide cDNA libraries. However, the quality and complexity of the library is likely a major factor determining how many potential targets can be selected out. Thus, one way to improve its selection efficiency would be to use libraries from various sources because some genes are only expressed under a certain circumstance or in a different tissue. For example, it is possible for maspin to be identified only from a normal breast library but not from the tumor library. Therefore, libraries suitable for use in the present invention may include, but not limited to, normal tissue libraries and libraries derived from breast tumors, lung tumors, stomach tumors, prostate tumors, colon tumors, pancreatic tumors, chronic lymphocytic leukemia, pituitary adenomas, uterine leiomyomas, or adult acute myeloid leukemia.

Moreover, to generate a 3'-UTR library in pSSMT-1, commercially available cDNA libraries may be used that were made from various tumor specimens or normal tissues or even cell lines. In particular, those libraries having cDNA inserts that can be easily released from the vectors by EcoRI and NotI and which are compatible with the cloning sites in pSSMT-1 are particularly useful. Most libraries are made using the oligo-dT as a primer during reverse transcription and should therefore carry the 3'-UTRs. In the illustrative examples discussed hereinbelow, cDNA libraries from tumor specimens were the primary UTR sources. However, given that a large set of genes involved in basic cellular processes can avoid microRNA regulation due to short 3'-UTRs, microRNA binding sites could be specifically depleted (71) or altered through alternative splicing. Furthermore, tumor cells tend to express different gene patterns than normal tissues. Therefore, it is also within the scope of the present invention to generate UTR libraries from normal cDNAs of corresponding tissues.

In an illustrative example, a 3'-UTR library was constructed by migrating a breast tumor cDNA library clone (Invitrogen) into the pSSMT-1 plasmid resulting in pSSMT-1-Lib (FIG. 2). One skilled in the art will also appreciate that, the 3'-UTR library hereof does not necessarily need to be a true 3'-UTR library because some clones carry complete gene coding sequences and it is believed that that an entire coding region plus the 3'-UTR carrying a microRNA target binding site is still able to respond to regulation by the microRNA (57). Furthermore, a library of this type permits a determination as to whether any sequences in addition to the 3'-UTR can be responsible for regulation by the target microRNA.

The expression cassette may also include an operator gene corresponding to the repressor. As an illustrative example, if tetracycline repressor (tetR) is being used then the corresponding operator gene, tetracycline operator (tetO) would be used. Suitable operator genes include, but are not limited to, tetO, LacO, and combinations thereof.

In certain embodiments, the operator gene may be operably linked to a promotor. In one embodiment, the transcriptional effector sequence is a mammalian promoter. In addition, the transcriptional effector can also include additional promoter sequences and/or transcriptional regulators, such as enhancer and silencers or combinations thereof. These transcriptional effector sequences can include portions known to bind to cellular components which regulate the transcription of any operably linked coding sequence. For example, an enhancer or silencer sequence can include sequences that bind known cellular components, such as transcriptional regulatory proteins. The transcriptional effector sequence can be selected from any suitable nucleic acid, such as genomic DNA, plasmid DNA, viral DNA, mRNA or cDNA, or any suitable organism (e.g., a virus, bacterium, yeast, fungus, plant, insect or mammal). It is within the skill of the art to select appropriate transcriptional effector sequences based upon the transcription and/or translation system being utilized. Any individual regulatory sequence can be arranged within the transcriptional effector element in a wild-type arrangement (as present in the native genomic order), or in an artificial arrangement. For example, a modified enhancer or promoter sequence may include repeating units of a regulatory sequence so that transcriptional activity from the vector is modified by these changes.

In certain embodiments of the present invention, the promoters are constitutive promoters. Constitutive promoters can be selected, e.g., from Rous sarcoma virus (RSV) long terminal repeat (LTR) promoter, cytomegalovirus immediate early gene (CMV) promoter, simian virus 40 early (SV40E) promoter, elongation factor 1 alpha promoter (EF1a), cytoplasmic beta-actin promoter, adenovirus major late promoter, and the phosphoglycerol kinase (PGK) promoter. In one embodiment, a constitutive promoter is a CMV promoter. In another embodiment, a constitutive promoter is an SV40E promoter.

The expression cassette hereof may further include an antibiotic-resistant gene which may, in turn, be operably linked to the promotor. Any antibiotic-resistant gene suitable for use in the present invention may be used including, but not limited to, puromycin, hygromycin, neomycin, zeocin, ampicillin, kanamycin, tetracycline, chloramphenicol, and combinations thereof.

In certain aspects, the present invention is also directed to a simple and efficient technique for identification of physiologic targets for microRNA. One of many advantages of this method is that it allows for identification of those targets that carry no conserved microRNA binding sites. Finally, this technique can be easily applied to identify targets for other microRNAs.

In particular, the genetic selection system of the present invention includes a method for identifying a protein as a target for a microRNA. This method includes a first step of introducing a plasmid into host cells wherein the plasmid includes an antibiotic-resistant gene under transcriptal regulation of an operator gene and a 3'-UTR cDNA library fragment under transcriptional regulation of a repressor gene corresponding to the operator gene. Next, a microRNA is introduced into the host cells which are then grown in the presence of an antibiotic corresponding to the antibiotic-resistant gene. The cells containing the microDNA and the 3'-UTR cDNA library fragment that are bound to each other can then express the antibiotic-resistant gene. The protein can then be identified based on the 3'-UTR cDNA fragment from the host cells that grows in the presence of the antibiotic.

In an illustrative example of the method of the present invention, the plasmid pSSMT-1 described hereinabove was constructed to carry tetO-Pu which is an element that codes for puromycin gene (puromycin-N-acetyl-transferase) under tet operator (tetO). This antibiotic-resistant gene is able to confer resistance to puromycin when no repressor (e.g., tetR) is bound on the tetO site. Thus, for example, when the pSSMT-1-Lib is introduced into 293T cells (chosen for high transfection efficiency and a low level of miR-21 expression), the transfected cells are expected to die in the presence of puromycin because, like pSSMT-1, the puromycin gene in pSSMT-1-Lib is repressed by tTR-KRAB (FIG. 3). However, when a miR-21 expressing vector is co-transfected into these cells, the cells with a cDNA clone carrying a miR-21 recognition site in pSSMT-1-Lib are expected to survive and form colonies in the presence of puromycin (FIG. 3). This is because miR-21 is capable of suppressing expression of tTR-KRAB by interacting with a potential miR-21 site. In contrast, no colony is formed for the vast majority of clones which do not carry a potential miR-21 recognition site, just like those of un-transfected cells.

In another embodiment of the method of the present invention, microRNAs are selected from a pre-microRNA collection against a specific target gene. One benefit of using a pre-microRNA collection is that microRNAs may be identifiable even though those microRNAs were not in the predicted list. For example, the following 12 genes were chosen for target validation (Table 2) because these genes: (1) play an important role in tumorigenesis or tumor resistance to chemotherapy/hormone therapy; (2) have been previously shown to be often aberrantly expressed in tumor specimens; and (3) are likely microRNA targets.

In this embodiment, the pre-microRNA collection is introduced into host cells by infection. After infection, each pSSMT1-xxx-UTR is introduced into these cells. Selection may be performed, for example, in the presence of 1.5 µg/ml puromycin. A slightly higher concentration than normal may be used to reduce the background from the vector control. Once survival colonies are visible, they are transferred to 24-well plates and expanded. These cells are then used as a source for extraction of genomic DNA. PCR is then carried out using the primers flanking the pre-microRNA to recover microRNA sequences. Those microRNAs are candidates that potentially target this specific gene. Thus, for each target gene, two selections are possible—one for vector control and another for a pre-microRNA clone.

To confirm that the recovered microRNAs are truly responsible for puromycin resistance in this embodiment of the selection system, each of the recovered microRNA clones are individually introduced in order to test against a single microRNA instead of the pre-microRNA collection. Once each microRNA clone is verified by puromycin resistance, it is then determined whether such a microRNA clone is able to silence the endogenous gene expression by a suitable analysis technique such as Western blot. It is also determined whether the microRNA clone it is a direct target for this microRNA or which region of the 3'-UTR sequence is responsible for microRNA regulation. Finally, it is determined whether an antisense oligo against a specific microRNA will have an opposite effect on the validated targets.

In contrast to target genes that have a small number of potential microRNAs, a microRNA usually has a large number of potential targets. Many microRNAs can have over a thousand of potential targets based on prediction methods. In order to determine how many of the targets are specifically regulated by a particular microRNA, a third embodiment of the method of the present invention is provided wherein the selection procedure is reversed (i.e., target genes are selected for against a specific microRNA). In this method, cDNAs carrying the 3'-UTR are first cloned into a selection plasmid to generate a 3'-UTR library. It is then determined how many target genes can be selected out from this 3'-UTR library by overexpression of a specific microRNA. Using this method allows for further validation of predicted targets as well as identification of new microRNA targets.

Moreover, using this method allows for the use of different types of UTR libraries for selection purposes in accordance with the methods of the present invention. In a tumor-specific UTR library, a UTR library specific to certain type of cancer, such as breast cancer, can be generated. These tumor specific primers can be cloned into pSSMT1 and used in the selection against a given microRNA. In a pathway specific UTR library, 3'UTR sequences are cloned into a lentivector downstream of the repressor open reading frame to generate miR-Select 3'UTR libraries. For example, initial collections may include 654 human kinase and ~200 phosphatase mRNA 3'UTRs, as the products of these genes are known to play key roles in cellular signaling, and disruption of these regulatory networks can lead to cancer.

In a genome-wide cDNA library, the selection plasmid ideally would carry only 3'-UTR sequences because microRNAs are believed to interact specifically with targets at the 3'-UTR. However, there is a technical challenge to separate the coding region from the 3'-UTR sequence during construction of a UTR library, i.e., a pool of cDNAs, because there is no experimental sequence border between the coding region and 3'-UTR. Thus, each 3'-UTR sequence must be individually cloned to construct such a library which could be cumbersome. Therefore, using the method of the present invention, it was theorized that cDNA carrying the 3'-UTR plus the coding region sequence is still able to be efficiently silenced by microRNAs. For comparison, tTR-KRAB was fused to the entire p27 coding region plus the 3'-UTR (pSSMT1-p27-UTR-1), to the part of p27 coding region plus the 3'-UTR (pSSMT1-p27-UTR-2), and to the 3'-UTR alone (pSSMT1-p27-UTR-3) (FIG. 14A), respectively. After transfection of 293T cells with these constructs along with miR-221 expression vector and selection in the presence of puromycin (1.0 µg/ml) for 5 days, remarkable number of viable cells was recovered for all three constructs (FIG. 14B). In contrast, very few viable cells were recovered from the vector control. Importantly, there was no significant difference in cell survival among three p27-UTR-containing constructs (FIG. 14B). Therefore, these results suggest that it is not necessary to generate a "pure" 3'-UTR library for microRNA suppression. In other words, it is feasible to use a 3'-UTR containing cDNA library as source to save time and costs for reagents. Additional benefits of this UTR containing library including enabling a determination as to whether microRNAs can interact with coding regions or 5'-UTR to silence gene expression.

To generate a 3'-UTR library in pSSMT-1, commercially available cDNA libraries may be used. For example, previously purchased several cDNA libraries made from various tumor specimens or normal tissues or even cell lines from Invitrogen may be used. In particular, their libraries can be made in pSPORT, and cDNA inserts can be easily released from the vectors by EcoRI and NotI, which are compatible with the cloning sites in pSSMT-1. Finally, all of the libraries may be made using the oligo-dT as a primer during reverse transcription, meaning that they all should carry the 3'-UTRs. In this embodiment of the present invention, cDNA libraries from tumor specimens are used as the primary UTR sources. However, given that a large set of genes involved in basic cellular processes can avoid microRNA regulation due to short 3'-UTRs, microRNA binding sites could be specifically depleted (71) or altered through alternative splicing. Furthermore, tumor cells tend to express different gene patterns than normal tissues. Therefore, one embodiment of the present invention also the generation of UTR libraries from normal cDNAs of corresponding tissues. In this embodiment, the cDNA library is first digested with EcoRI and NotI and most of inserts ranging from 0.5 to 3.0 kb can be isolated after gel separation. The pooled cDNA fragments can then be ligated to the EcoRI and NotI-digested pSSMT-1. After transformation, colonies formed on LB plates can be pooled and plasmid DNA can be isolated.

In certain embodiments, the present invention also contemplates a kit for for identifying a protein as a target for a microRNA or for selecting microRNAs from a pre-microRNA collection against a specific target gene. The kit may include, but is not limited to, an expression cassette comprising at least one repressor, at least one 3'-UTR cDNA library fragment operably linked to the repressor, an operator gene corresponding to the repressor which is operably linked to a constitutive promotor, and an antibiotic resistance gene operably linked to the constitutive promotor.

EXAMPLES

The following non-limiting examples are provided to further illustrate the present invention.

Example 1

Construction of pSSMT-1

Referring now to FIG. 1, a pGL3 control vector (Promega) was used as a backbone to construct pSSMT-1. pGL3 vector control was digested with NotI, followed by filling with Klenow and self-ligation to eliminate the NotI site. The purpose of this step was to introduce a new NotI site downstream of tTR-KRAB to facilitate ligation of cDNA clones from the breast tumor library (in pCMV-SPORTS from Invitrogen) at a later stage. The modified vector was then digested with Hind3 and Kpn1 to remove the 240 bp SV40 promoter and insert the self-annealed adaptor sequences pGL3-Adaptor-5 (5'-CTTGGGATTTGAATAGGAA CCTGCAGGT) and pGL3-Adaptor-3 (5'-AGCTA CCTGCAGGTTCCTATTCAAATC CCAAGGTAC) through which a Sbf1 site (underlined) was introduced to accommodate the tTR-KRAB fragment carrying Kpn1 at one end and Sfb1 on the other end. To introduce the tet operator element (tetO), tetO was amplified using primers TRE-Bgl2-5.2 (AGGCGTATCACGAGGCCCTTTCG AGATCTAGTTTACCACTCCCTATCAGT, where Bgl2 was underlined) and TRE-Spe1-3.1 (TT ACTAGTGCGGAGGCTGGAT, where Spe1 was underlined) from pTRE (Clontech). This tetO element that ended with Bgl2 and Spe1, along with CMV promoter-Pu (1.2 kb) derived from pFIV-puro H1 (System Biosciences) which ended with Spe1 and SalI was ligated to the modified vector at BamHI and SalI sites by a three way ligation, resulting in pGL3 control-tetO-Pu. Thereafter, the PCR-amplified tTR-KRAB fragment was cloned into Sfb1 and Kpn1 sites of pGL3 control-tetO-Pu. During PCR amplification, EcoRI and NotI sites were introduced. The resultant plasmid was named pSSMT-1 which stands for selection system for microRNA targets.

Example 2

Construction of pSSMT-1-Lib

A 3'-UTR library was constructed by migrating a breast tumor cDNA library clones (Invitrogen) into pSSMT-1, resulting in pSSMT-1-Lib (FIG. 2). Although this is not a true 3'-UTR library because some clones carry complete gene coding sequences, a previous study suggests that an entire coding region plus the 3'-UTR carrying a miR-21 binding site is able to respond to regulation by miR-21 (Zhu et al, J Biol Chem 2007; 282:14328-14336). Furthermore, this library allows for determination of whether any sequences in addition to the 3'-UTR are responsible for regulation by miR-21.

Referring now to FIG. 2, a commercially available cDNA library expected to contain fragments to carry protein-coding sequences, was subcloned into pSSMT-1 to generate pSSMT-1-Lib. In particular, a breast tumor cDNA library made in pCMV-SPORTS (Invitrogen) was digested with EcoRI and NotI. The cDNA library was digested with EcoRI and NotI and most of the inserts ranging from 0.5 to 3.0 kb were isolated after gel separation. The pooled cDNA fragments were then ligated to the EcoRI and NotI-digested pSSMT-1. After transformation, colonies formed on LB plates were pooled and plasmid DNA was isolated. After separation in an agarose gel, fragments ranging from 0.5 to 3 kb were isolated, purified and finally ligated to pSSMT-1 at EcoRI and NotI, resulting in pSSMT-1-Lib. Over 40,000 colonies were obtained through this procedure and the quality of this library was determined by isolating randomly picked colonies and restriction digestion. Over 90% of colonies carry an insert with size ranging from 0.5 kb to 2.5 kb.

Example 3

Enforced Expression of miR-21

PCR was then used to amplify the pre-miR-21 contained in DNA fragments from MCF-10A genomic DNA as described previously (Zhu et al, J Biol Chem 2007; 282:14328-14336), and the expression of mature miR-21 was confirmed by TaqMan real-time PCR.

Example 4

Transfection

Plasmid DNA was introduced into cells by the calcium phosphate method as described previously (Mo et al., J Biol Chem 2000; 275:41107-41113). Briefly, cells were seeded in 10 cm dishes 2 h before transfection. The transfection efficiency was monitored by sparking a ⅒ EGFP vector. In most cases, the transfection rate was about 75%. One day after transfection, the cells were split from one to two dishes. Once cells were attached, puromycin was added at 1.0-1.5 µg/ml. To suppress miR-21 expression, a locked nucleic acid (LNA) anti-miR-21 oligo was used. To monitor the localization of the oligo, it was labeled with FAM, a green fluorescent dye. The transfection of LNA-anti-miR-21 was carried out using RNAfectin (Applied Biological Materials, British Columbia, Calif.) per the manufacturer's protocol.

When pSSMT-1-Lib is introduced into 293T cells, the transfected cells are expected to die in the presence of puromycin because like pSSMT-1, the puromycin gene in pSSMT-1-Lib is repressed by tTR-KRAB (FIG. 3). 293T cells were chosen because of their high transfection efficiency and low level of miR-21 expression (not shown). However, when the miR-21 expressing vector is co-transfected into these cells, the cells with a cDNA clone carrying a miR-21 recognition site in pSSMT-1-Lib are expected to survive and form colonies in the presence of puromycin (FIG. 3). This is because miR-21 is capable of suppressing expression of tTR-KRAB by interacting with a potential miR-21 site. In contrast, no colonies are formed for the vast majority of clones which do not carry a potential miR-21 recognition site, similarly to un-transfected cells.

Example 5

Selection

After transfection, the cells were grown at 1-1.5 µg/ml puromycin. New medium with fresh puromycin was changed every other day. Two weeks later, when colonies were formed, they were transferred to 24-well plates for further growth. To determine whether the surviving colonies carried a potential miR-21 target sequence from the library, genomic DNA was extracted from these cells and PCR was carried out to amplify potential sequences using primers Krab-Lib-5.2 (5'-TTCA-GAGACTGCATTTGAAATC) and Krab-Lib-3.2 (5'-TGC-CAAGCTACCTGCAGGTTG) derived from known sequences from the vector (FIG. 4). The PCR products were re-cloned into pSSMT-1 to determine whether they still conferred resistance to puromycin. At this point, each of the potential clones was tested individually. The positive clones were selected and re-tested by luciferase assays by subcloning them into the pGL3-control vector. Finally, the clones, which tested positive both by puromycin resistance tests and luciferase assays, were sequenced following the selection procedure shown in FIG. 5.

Example 6

Suppression

Figure 6A:
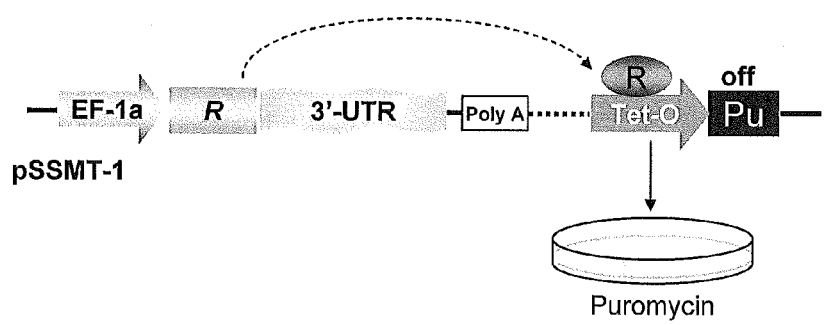
FIG. 6A is a schematic representation of validation of miR-21 target TPM1 by the selection system in accordance with one embodiment of the present invention.
Figure 6B:
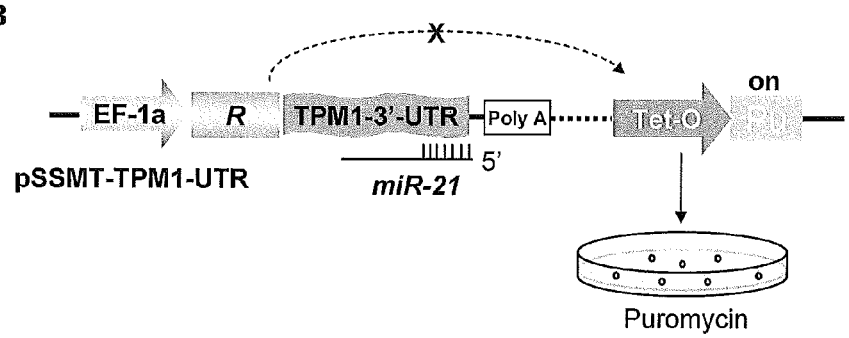
FIG. 6B is a schematic representation of validation of miR-21 target TPM1 by the selection system in accordance with another embodiment of the present invention.
Figures 7A, 7B:
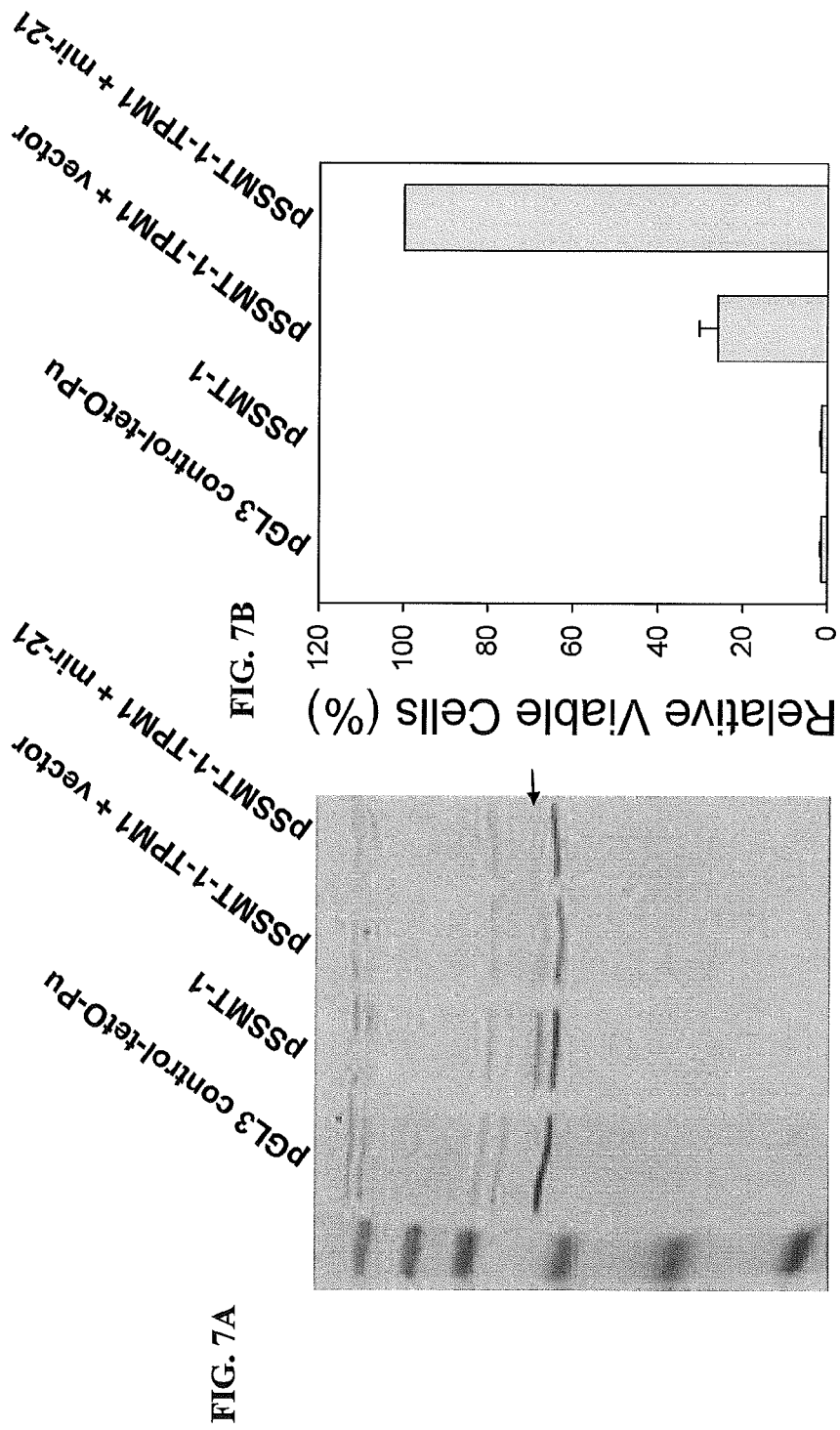
FIG. 7A is a western blot showing validation of miR-21 target TPM1 by the selection system in accordance with one embodiment of the present invention.
FIG. 7B is a graphical representation of the western blot of FIG. 7A.

To determine whether any sequence downstream of tTR-KRAB can suppress tTR-KRAB expression such that it confers resistance to puromycin, tropomyosin 1 (TPM1) 3'-UTR which carries a known miR-21 binding site was cloned into pSSMT-1 (FIG. 6) since it was shown to be functional and respond to miR-21 regulation (Zhu et al, J Biol Chem 2007; 282:14328-14336). Firstly, a Western blot was performed to determine whether tTR-KRAB is suppressed by TPM1-UTR. As shown in FIG. 7A, a 38 kDa band corresponding to tTR-KRAB fusion protein was detected in cells transfected with pSSMT-1, but the level of this protein was reduced in the cells transfected with pSSMT-1-TPM1-UTR, likely due to the endogenous miR-21. Overexpression of miR-21 further reduced the level of tTR-KRAB. Consistent with this result, it was found that the cells transfected with pSSMT-1-TPM1-UTR plus miR-21 were more resistant to puromycin than those transfected with pSSMT-1-TPM1-UTR plus vector control (FIG. 7B). In contrast, the cells transfected with either pGL3 control-tetO-Pu or pSSMT-1 were very sensitive to puromycin. Therefore, miR-21 specifically inhibited the protein level of tTR-KRAB and made cells more resistant to puromycin, demonstrating the feasibility of this system.

Example 7

Isolation

Through the selection procedures as described in FIG. 5, a total of 14 putative miR-21 targets were isolated as shown in Table 1. Two of them were programmed cell death 4 (PDCD4) and maspin proteins, which have previously been implicated in tumorigenesis and metastasis (Cmarik et al., Proc Natl Acad Sci USA 1999; 96:14037-14042) or carcinogenesis (Lau et al., Cancer Res 2007; 67:2107-2113). Furthermore, both PDCD4 and maspin carry a predicted miR-21 binding side (FIG. 8) based on two miRNA target predicting programs, "program miRBase target" (http://microrna.sanger.ac.uk) or Targetscan (http://www.targetscan.org/). The luciferase reporter carrying the PDCD4 3'-UTR revealed about 60% reduction of luciferase activity by miR-21 compared to the vector control (FIG. 8); deletion of the putative miR-21 binding site abolished the effect (data not shown). To further determine the regulation by miR-21, we cloned the PDCD4 3'-UTR into a modified GFP vector as described in Zhu et al, J Biol Chem 2007; 282:14328-14336. In addition, we made a similar finding for maspin (FIGS. 8 C and D).

On the other hand, although cytokeratin 8 caries no conserved miR-21 binding site, a two-dimensional in gel differentiation (2-DIGE) analysis indicated that this gene was upregulated by anti-miR-21 oligonucleotide (not shown), also suggesting cytokeratin 8 as a miR-21 target. Thus, the 3'-UTR of cytokeratin 8 was cloned into the pGL3 control vector. The luciferase activity from Luc-cytokeratin 8 UTR was specifically suppressed by miR-21 (FIG. 9A). Similarly, downregulation of the GFP protein by miR-21 was detected when this cytokeratin 8 UTR was cloned downstream of GFP (FIG. 9B).

Figures 10A, 10B:
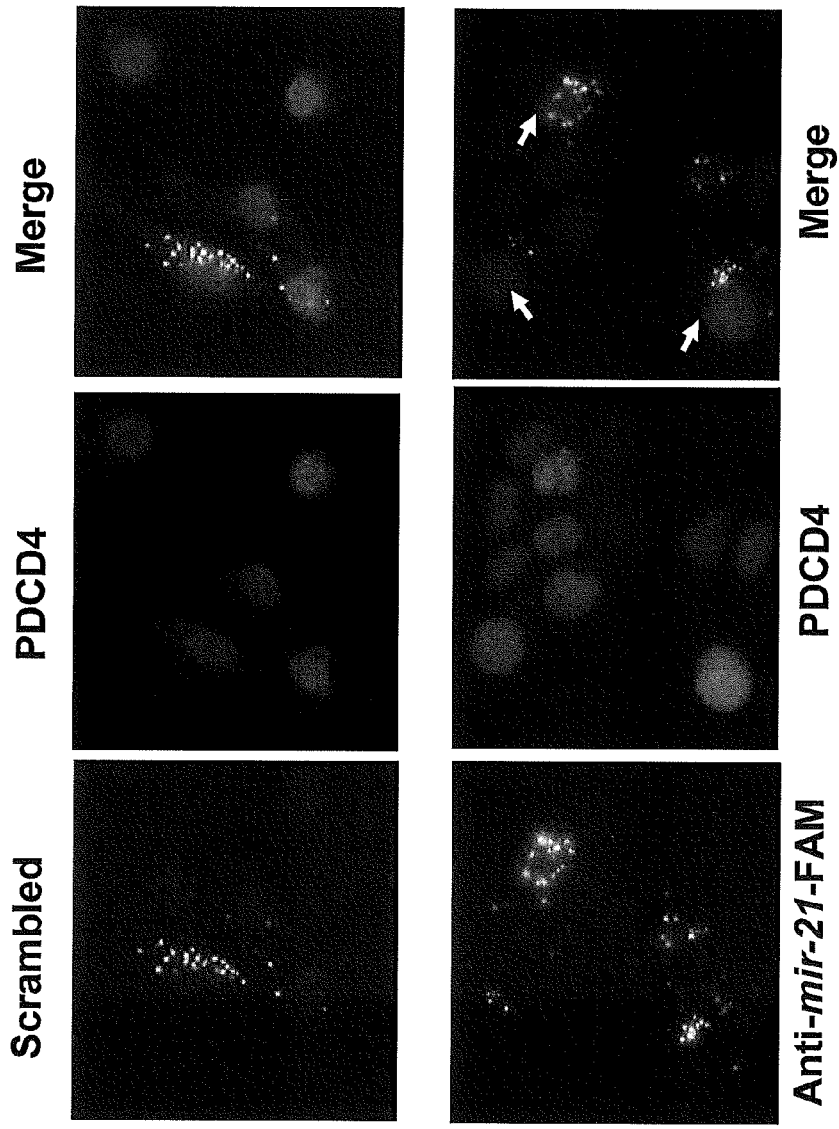
FIG. 10A is an immunostain that demonstrates transfected MCF-7 cells with locked nucleic acid LNA anti-miR-21 oligo and then immunostained with anti-PDCD4 antibody.
FIG. 10B is an immunostain that demonstrates non-transfected MCF-7 cells.

To better characterize the effect of miR-21 on PDCD4 expression, MCF-7 cells were transfected with locked nucleic acid LNA anti-miR-21 oligo and then immunostained with anti-PDCD4 antibody. Since the anti-miR-21 was labeled with FAM, it was easy to detect the transfection. As expected, anti-miR-21 was predominantly localized to stress bodies (puncture like structures) (FIG. 10B). In addition, the transfected cells expressed higher levels of PDCD4 than the untransfected ones (FIG. 10B). In contrast, scrambled oligos did have not any effect on PDCD4 expression (FIG. 10A).

Example 8

Western Blot

Figure 11B:
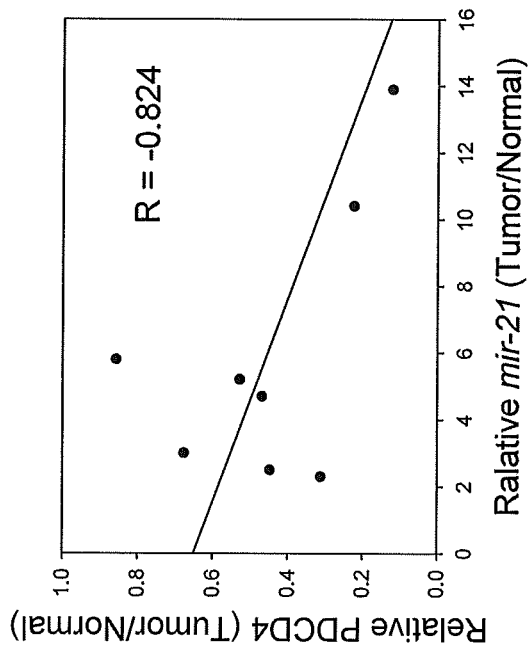
FIG. 11B is a graphical representation of a statistical analysis using the Pearson's method confirming the inverse correlation between PDCD4 protein and miR-21 in the tissue samples of FIG. 11A with a correlation coefficient of −0.824.
Figure 11A:
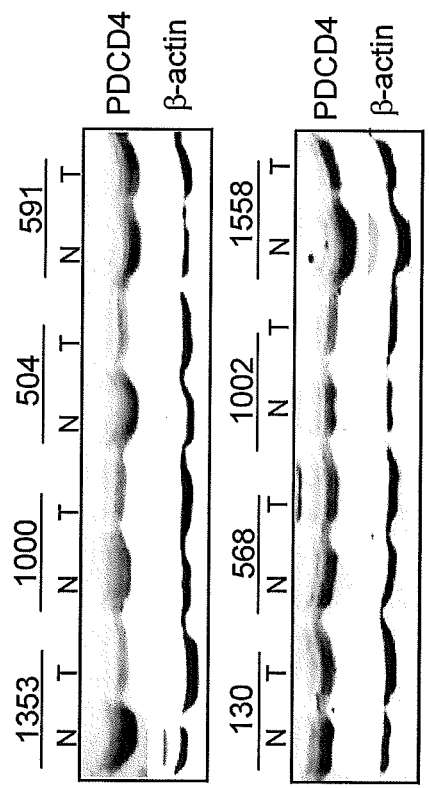
FIG. 11A is a western blot showing PDCD4 protein levels in 8 pairs of matched breast tumor specimens.

To determine the clinical significance of miR-21 target genes, PDCD4 protein levels in 8 pairs of matched breast tumor specimens were examined by Western blotting. As expected, lower levels of PDCD4 were detected in tumors in all cases (FIG. 11A). To determine whether there is any correlation between PDCD4 and miR-21, miR-21 expression was also measured in these samples by TaqMan real-time PCR. The findings indicated that all tumors revealed higher levels of miR-21 expression. Statistical analysis using the Pearson's method confirmed the inverse correlation between PDCD4 protein and miR-21 in these tissue samples, with a correlation coefficient of −0.824 (FIG. 11B). Protein was extracted as described previously (Zhu et al, J Biol Chem 2007; 282:14328-14336) and the concentration was determined by Protein assays kit (Bio-Rad). Protein separation and immunoblot were carried out according to standard methods.

Example 9

Immunofluoresence Microscopy

Figures 12A, 12B:
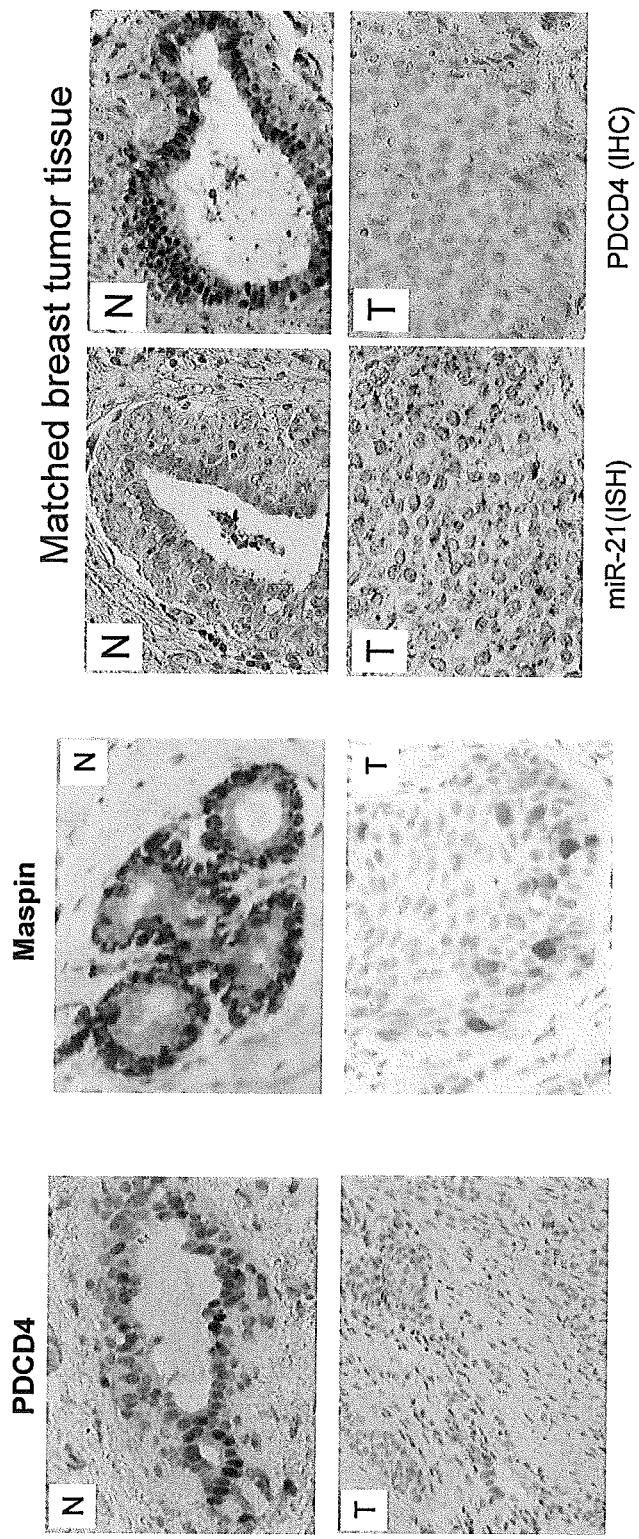
FIG. 12A is an immunohistochemical stain showing a negative correlation between miR-21 and PDCD4 in matched breast tumor specimens.
FIG. 12B is an in situ hybridization of the tumor specimens of FIG. 12A.

Finally, this inverse relationship was examined at the cellular levels by immounohsitochemistry (IHC) and in situ hybridization (ISH). As shown in FIG. 12, both PDCD4 and maspin were highly expressed in normal breast tissue (N), but lowly expressed in tumor tissue (T). In contrast, miR-21 level was low in normal tissue, but high in breast tumor tissues.

Together, these results suggest that PDCD4, maspin and cytokeratin 8 are physiologic targets for miR-21, demonstrating the feasibility of this selection system for miRNA targets. Given the importance of miR-21 in cancer, identification of these targets provides new insight into molecular mechanisms of miR-21-mediated gene expression and tumorigenesis. Thus, as an oncogenic microRNA, miR-21 may exert its function through suppression of tumor suppressor genes like PDCD4 or maspin and special cytoskeletal proteins like cytokeratin 8, in addition to the previously identified TPM1 (Zhu et al, J Biol Chem 2007; 282:14328-14336).

Immunofluoresence staining was used to determine PDCD expression in anti-miR-21 transfected cells as previously described (Wu et al., Mol Cancer Ther 2007; 6:1823-1830). Briefly, MCF-7 were transfected with scrambled and were fixed with 3% paraformaldehyde. Primary antibody against PDCD (Rockland) was used to detect the PDCD signal, followed by a secondary antibody conjugated with Alexa Fluor 560.

Paraffin-embedded tissue was pretreated at 65° C. for 2 h, followed by deparaffinization using standard procedures. Antigen retrieval was carried out in antigen retrieval solution (10 mM Tris, 1 mM EDTA, pH9.0) before applying the primary Ubc9 antibody. Thereafter, the slides were incubated for 2 h at room temperature followed by extensive washes with PBST and further incubated for 1 h at room temperature with the secondary antibody conjugated with horse radish peroxidase (HRP). HRP activity was detected using Histostain Plus kit (Invitrogen) according to the manufacturer's instruction. Finally, sections were counterstained with hematoxylin and mounted.

Having described the invention in detail, those skilled in the art will appreciate that modifications may be made of the invention without departing from the spirit and scope thereof. Therefore, it is not intended that the scope of the invention be limited to the specific embodiments described. Rather, it is intended that the appended claims and their equivalents determine the scope of the invention.

We claim:

1. A nucleic acid expression cassette expressible in mammalian cells, wherein the expression cassette comprises the following elements in a 5' to 3' direction: a) a promoter; b) a repressor operably linked to the promoter; c) a 3'-UTR cDNA library fragment including mRNA of the 3'-UTR cDNA library sequence operably linked to the repressor; d) an operator gene corresponding to the repressor, which is operably linked to a constitutive promoter, and e) an antibiotic-resistant element operably linked to the constitutive promoter, wherein the mRNA encoding the repressor comprises a fusion mRNA that also includes the mRNA of the 3'-UTR cDNA library fragment.

2. The expression cassette of claim 1, wherein the repressor is selected from the group consisting of tetracycline repressor (tetR), LacI, and combinations thereof.

3. The expression cassette of claim 2, wherein the repressor is tetR.

4. The expression cassette of claim 1, wherein the 3'-UTR cDNA library is selected from the group consisting of breast tumor cDNA libraries, normal cDNA libraries, other tumor cDNA libraries, and combinations thereof.

5. The expression cassette of claim 1, wherein the antibiotic-resistant element is selected from the group consisting of puromycin, hygromycin, neomycin, zeocin, ampicillin, kanamycin, tetracycline, chloramphenicol, and combinations thereof.

6. The expression cassette of claim 1, wherein the constitutive promoter is selected from the group consisting of retroviral Rous sarcoma virus (RSV) long terminal repeat (LTR) promoter, cytomegalovirus immediate early gene (CMV) promoter, elongation factor 1 alpha promoter (EF1a), simian virus early (SV40) promoter, cytoplasmic beta-actin promoter, adenovirus major late promoter, and phosphoglycerol kinase (PGK) promoter.

7. The expression cassette of claim 6, wherein the constitutive promoter is CMV promoter.

8. The expression cassette of claim 1, wherein the expression cassette is contained in a plasmid, shuttle vector, or viral vector.

9. A nucleic acid expression cassette expressible in mammalian cells, wherein the expression cassette comprises the following elements in a 5' to 3' direction: a) a promoter; b) a fusion gene of tetracycline repressor and Krab gene operably linked to the promoter; c) a 3'-UTR cDNA library fragment including mRNA of the 3'-UTR cDNA library sequence operably linked to the fusion gene; d) a tetracycline operator gene operably linked to a constitutive promoter, and e) an antibiotic-resistant element operably linked to the constitutive promoter, wherein the mRNA encoding the repressor comprises a fusion mRNA that also includes the mRNA of the 3'-UTR cDNA library fragment.

10. The expression cassette of claim 9, wherein the 3'-UTR cDNA library is selected from the group consisting of breast tumor cDNA libraries, normal cDNA libraries, other tumor cDNA libraries, and combinations thereof.

11. The expression cassette of claim 9, wherein the antibiotic-resistant element is selected from the group consisting of puromycin, hygromycin, neomycin, zeocin, ampicillin, kanamycin, tetracycline, chloramphenicol, and combinations thereof.

12. The expression cassette of claim 9, wherein the constitutive promoter is selected from the group consisting of retroviral Rous sarcoma virus (RSV) long terminal repeat (LTR) promoter, cytomegalovirus immediate early gene (CMV) promoter, simian virus early (SV40) promoter, cytoplasmic beta-actin promoter, adenovirus major late promoter, and phosphoglycerol kinase (PGK) promoter.

13. The expression cassette of claim 12, wherein the constitutive promoter is CMV promoter.

14. A mammalian cell that is transformed with the expression cassette of claim 1.

15. The mammalian cell of claim 14, wherein the mammalian cell is selected from the group consisting of HEK293, HT1080, NTERA-2D, HeLa, Caco2, HepG2, BALBC/3T3, MCF-7 and MDA-MB-231, and Cos-7.

16. A method for identifying a protein as a target for a microRNA, the method comprising: a) introducing into host cells a plasmid comprising a promoter, an antibiotic-resistant element under transcriptional regulation of an operator gene and a 3'-UTR cDNA library fragment including mRNA of the 3'-UTR cDNA library sequence under transcriptional regulation of a repressor corresponding to the operator gene; b) introducing into the host cells the microRNA; c) growing the host cells in the presence of the antibiotic, wherein the cells which contain the microRNA and the 3'-UTR cDNA library fragment that bind to each other can express the antibiotic-resistant element; d) identifying the protein based on the 3-UTR cDNA fragment from the host cells that can grow in the presence of the antibiotic, wherein the mRNA encoding the repressor comprises a fusion mRNA that also includes the mRNA of the 3'-UTR cDNA library fragment.

17. The method of claim 16, wherein the repressor is selected from the group consisting of tetracycline repressor (tetR) gene, LacI, and combinations thereof.

18. The method of claim 17, wherein the repressor is tetracycline repressor (tetR) gene.

19. The method of claim 16, wherein the microRNA is selected from the group consisting of miR-21, miR-15, miR-16, let-7, miR-17-5p, miR-20a, miR-372, miR-373, miR-335, miR-10b, miR-30, and miR-224.

20. The method of claim 19, wherein the microRNA is selected from the group consisting of miR-21, miR-15, miR-16, let-7, miR-17-5p, miR-20a, miR-372, miR-373, miR-335, miR-10b, miR-30, and miR-224.

21. The method of claim 16, wherein the host cells are selected from HEK293, HT1080, NTERA-2D, HeLa, Caco2, HepG2, BALBC/3T3, MCF-7 and MDA-MB-231, and Cos-7.

22. The method of claim 16, wherein the 3'-UTR cDNA library is selected from the group consisting of breast tumor cDNA libraries, normal cDNA libraries, other tumor cDNA libraries, and combinations thereof.

23. The method of claim 16, wherein the antibiotic-resistant element is an element that codes for genes selected from the group consisting of puromycin, hygromycin, neomycin, zeocin, ampicillin, kanamycin, tetracycline, and chloramphenicol.

24. The method of claim 16, wherein the step of identifying the protein is selected from the group consisting of PCR, Western blotting, immunohistochemistry and immunofluorescence microscopy.

25. A method for identifying a protein as a target for a microRNA, the method comprising: a) introducing into host cells a plasmid comprising a promoter, an antibiotic-resistant element under transcriptional regulation of tetracycline operator (tetO) gene and a 3'-UTR cDNA library fragment including mRNA of the 3'-UTR cDNA library sequence under transcriptional regulation of tetracycline repressor (tetR) gene; b) introducing into the host cells the microRNA; c) growing the host cells in the presence of the antibiotic, wherein the cells which contain the microRNA and the 3'-UTR cDNA library fragment that bind to each other can express the antibiotic-resistant element; d) identifying the protein based on the 3-UTR cDNA fragment from the host cells that can grow in the presence of the antibiotic, wherein the mRNA encoding the repressor comprises a fusion mRNA that also includes the mRNA of the 3'-UTR cDNA library fragment.

26. The method of claim 25, wherein the microRNA is selected from the group consisting of miR-21, miR-15, miR-16, let-7, miR-17-5p, miR-20a, miR-372, miR-373, miR-335, miR-10b, miR-30, and miR-224.

27. The method of claim 26, wherein the microRNA is selected from the group consisting of miR-21, miR-15, miR-16, let-7, miR-17-5p, miR-20a, miR-372, miR-373, miR-335, miR-10b, miR-30, and miR-224.

28. The method of claim 25, wherein the host cells are selected from HEK293, HT1080, NTERA-2D, HeLa, Caco2, HepG2, BALBC/3T3, MCF-7 and MDA-MB-231, and Cos-7.

29. The method of claim 25, wherein the 3'-UTR cDNA library is selected from the group consisting of breast tumor cDNA libraries, normal cDNA libraries, other tumor cDNA libraries, and combinations thereof.

30. The method of claim 25, wherein the antibiotic-resistant element is an element that codes for a gene selected from the group consisting of puromycin, hygromycin, neomycin, zeocin, ampicillin, kanamycin, tetracycline, and chloramphenicol.

31. The method of claim 25, wherein the step of identifying the protein is selected from the group consisting of PCR, Western blotting, immunohistochemistry, and immunofluorescence microscopy.

32. A kit comprising the expression cassette of claim 1.

33. The kit of claim 32, wherein the repressor is tetR.

34. The kit of claim 32, wherein the 3'-UTR cDNA library is selected from the group consisting of breast tumor cDNA libraries, normal cDNA libraries, other tumor cDNA libraries, and combinations thereof.

35. The kit of claim 32, wherein the antibiotic-resistant element is selected from the group consisting of puromycin, hygromycin, neomycin, zeocin, ampicillin, kanamycin, tetracycline, and chloramphenicol.

* * * * *